(12) United States Patent
Nishida et al.

(10) Patent No.: US 10,689,318 B2
(45) Date of Patent: Jun. 23, 2020

(54) BISPHENOL HAVING FLUORENE SKELETON, METHOD FOR PRODUCING SAME, POLYARYLATE RESIN, (METH)ACRYLATE COMPOUND AND EPOXY RESIN WHICH ARE DERIVED FROM THE BISPHENOL

(71) Applicant: TAOKA CHEMICAL CO., LTD., Osaka-shi, Osaka (JP)

(72) Inventors: Yuji Nishida, Osaka (JP); Takafumi Saiki, Osaka (JP); Ayumi Matsushima, Osaka (JP); Hideki Morio, Osaka (JP); Yuka Morinaga, Osaka (JP); Yoshinori Kawamura, Osaka (JP)

(73) Assignee: TAOKA CHEMICAL CO., LTD., Osaka-shi (JP)

( * ) Notice: Subject to any disclaimer, the term of this patent is extended or adjusted under 35 U.S.C. 154(b) by 126 days.

(21) Appl. No.: 16/074,895

(22) PCT Filed: Jan. 25, 2017

(86) PCT No.: PCT/JP2017/002551
§ 371 (c)(1),
(2) Date: Aug. 2, 2018

(87) PCT Pub. No.: WO2017/135123
PCT Pub. Date: Aug. 10, 2017

(65) Prior Publication Data
US 2019/0055180 A1    Feb. 21, 2019

(30) Foreign Application Priority Data

Feb. 3, 2016  (JP) .................. 2016-018952
Mar. 2, 2016  (JP) .................. 2016-039488

(Continued)

(51) Int. Cl.
  *C07C 39/15*   (2006.01)
  *C07C 39/17*   (2006.01)
  (Continued)

(52) U.S. Cl.
  CPC .............. *C07C 39/17* (2013.01); *C07C 37/48* (2013.01); *C07C 43/23* (2013.01); *C07C 67/40* (2013.01);
  (Continued)

(58) Field of Classification Search
  None
  See application file for complete search history.

(56) References Cited

U.S. PATENT DOCUMENTS 5,110,993 A * 5/1992 Hay .................. C07C 39/17
                                              568/716
2012/0029244 A1  2/2012 Fujii et al.
(Continued)

FOREIGN PATENT DOCUMENTS

CN   103012759 A   4/2013
JP   S63-218725 A  9/1988
(Continued)

OTHER PUBLICATIONS

International Search Report for PCT/JP2017/002551 (PCT/ISA/210) dated Apr. 25, 2017.
(Continued)

*Primary Examiner* — Richard A Huhn
(74) *Attorney, Agent, or Firm* — Birch, Stewart, Kolasch & Birch, LLP

(57) ABSTRACT

Provided are a bisphenol represented by the general formula (1), a method for producing the bisphenol, and a polyarylate resin, a (meth)acrylate compound and an epoxy resin which are derived from the bisphenol. In the formula (1), $R_1$ to $R_4$ are the same or different, and each represent an alkyl group, (Continued)

an aryl group or a halogen atom, $n_1$ and $n_2$ are the same or different, and each represent an integer of 1 to 4, and $k_1$ to $k_4$ are the same or different, and each represent 0 or an integer of 1 to 4. When at least one of $k_1$ to $k_4$ is 2 or more, corresponding $R_1$ to $R_4$ may be the same or different.

23 Claims, 9 Drawing Sheets

(30) Foreign Application Priority Data

Aug. 9, 2016 (JP) .................. 2016-156053
Dec. 8, 2016 (JP) .................. 2016-238786

(51) Int. Cl.

| | | |
|---|---|---|
| C07C 39/21 | (2006.01) | |
| C07C 39/23 | (2006.01) | |
| C08G 75/20 | (2016.01) | |
| C08F 22/14 | (2006.01) | |
| C07C 43/23 | (2006.01) | |
| C08G 63/193 | (2006.01) | |
| C08F 122/10 | (2006.01) | |
| C07C 37/48 | (2006.01) | |
| C07C 67/40 | (2006.01) | |
| C07C 69/54 | (2006.01) | |
| C08F 122/14 | (2006.01) | |
| C08G 59/24 | (2006.01) | |
| C08G 63/197 | (2006.01) | |
| G02B 1/04 | (2006.01) | |

(52) U.S. Cl.
CPC ........ *C07C 69/54* (2013.01); *C08F 122/1006* (2020.02); *C08F 122/14* (2013.01); *C08G 59/245* (2013.01); *C08G 63/193* (2013.01); *C08G 63/197* (2013.01); *G02B 1/04* (2013.01); *C07C 39/15* (2013.01); *C07C 39/21* (2013.01); *C07C 39/23* (2013.01); *C07C 2603/18* (2017.05); *C08G 75/20* (2013.01)

(56) References Cited

U.S. PATENT DOCUMENTS

| | | | |
|---|---|---|---|
| 2014/0166105 A1 | 6/2014 | Kawakami et al. | |
| 2015/0025215 A1* | 1/2015 | Kim | C07C 43/23 528/194 |

FOREIGN PATENT DOCUMENTS

| | | | |
|---|---|---|---|
| JP | H04-325508 A | | 11/1992 |
| JP | 2001-206863 A | | 7/2001 |
| JP | 2002-088136 A | | 3/2002 |
| JP | 2004-83855 A | | 3/2004 |
| JP | 2006-152115 A | | 6/2006 |
| JP | 2007-91870 A | | 4/2007 |
| JP | 2009-235196 A | | 10/2009 |
| JP | 2010-018753 A | | 1/2010 |
| JP | 2011-246583 A | | 12/2011 |
| JP | 2012-131865 A | | 7/2012 |
| JP | 2013-067146 A | | 4/2013 |
| JP | 2014-231512 A | | 12/2014 |
| JP | 2014237602 A | * | 12/2014 |
| JP | 2018076419 A | * | 5/2018 |
| TW | 200403269 A | | 3/2004 |
| TW | 201036942 A1 | | 4/2013 |

OTHER PUBLICATIONS

Wang et al., "Synthesis of Poly(arylene Ether)s Based on 9,9-Bis(3,5-Diphenyl-4-Hydroxyphenyl) fluorene", Journal of Polymer Science: Part A: Polymer Chemistry, vol. 29, 1991, pp. 1045-1052.

* cited by examiner

BISPHENOL HAVING FLUORENE SKELETON, METHOD FOR PRODUCING SAME, POLYARYLATE RESIN, (METH)ACRYLATE COMPOUND AND EPOXY RESIN WHICH ARE DERIVED FROM THE BISPHENOL

TECHNICAL FIELD

The present invention relates to a bisphenol having a novel fluorene skeleton having a phenyl group as a substituent, a method for producing the bisphenol, a polyarylate resin, a (meth)acrylate compound and an epoxy resin which are derived from the bisphenol, and a method for producing the polyarylate resin, the (meth)acrylate compound and the epoxy resin.

BACKGROUND ART

Recently, for optical members (e.g. prism sheets, overcoating agents, hard coating agents, antireflection films or optical films, optical sheets, optical fibers, optical waveguides, holograms, films for liquid crystals, films for organic EL, various optical lenses and the like, which are used for liquid crystal display devices), various transparent resins (polycarbonate, polyester and the like) are frequently used in view of advantages such as favorable molding processability and high productivity or weight reduction and thickness reduction. From the viewpoint of thickness reduction of the optical members, the resins are required to have a further high refractive index.

Among these various transparent resins, resins in which a bisphenol having a fluorene skeleton is used as a raw material monomer have attracted attention as transparent resins for optical members in recent years because they have a high refractive index, and are excellent in heat resistance etc. Among them, resins produced from a bisphenol having a structure represented by the following formula (5):
[Chemical Formula 1]

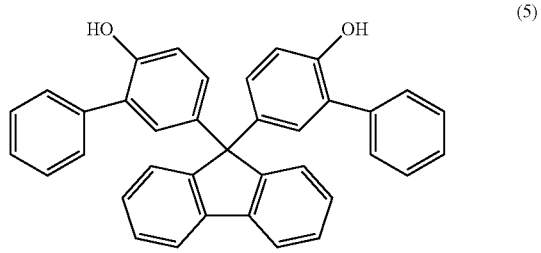 [SMILES: Oc1ccc(C2(c3ccc(O)c(-c4ccccc4)c3)c3ccccc3-c3ccccc32)cc1-c1ccccc1]

(5)

and having a phenyl group as a substituent are known to have a particularly high refractive index and exhibit excellent heat resistance (e.g. PTDs 1 and 2).

However, the bisphenol represented by the formula (5) has a very high melting point of about 270° C., and thus has the problem that the bisphenol is difficult to handle as a resin raw material. In particular, in the case of a melting polymerization method or the like in which a resin is produced without using a solvent, it is normally necessary to melt a raw material once with the reaction temperature set to a temperature higher than or equal to the melting point of the raw material at the time of carrying out a polymerization reaction, and therefore a bisphenol having a high melting point is used as a raw material, there is the problem that the reaction temperature must be increased, and thus the resin is easily colored during the reaction.

In addition, as resins that can be used for the above-mentioned optical members, for example, polyarylate resins, resins obtained by curing (polymerizing) a curable composition containing a (meth)acrylate compound, and the like are known.

The polyarylate resin is a thermoplastic wholly aromatic polyester having a constituent unit derived from a bisphenol and a constituent unit derived from an aromatic dicarboxylic acid, and has characteristics such as relatively high heat resistance, high transparency and a high refractive index.

As a polyarylate resin having a high refractive index among the above-mentioned polyarylate resins, for example, PTD 3 discloses a polyarylate resin having a constituent unit derived from 9,9-bis(hydroxy-fused polycyclic aryl)fluorene, and a constituent unit derived from an aromatic dicarboxylic acid, and the polyarylate resin has a very high refractive index of 1.71 to 1.74. However, the polyarylate resin has a very high glass transition temperature of 312 to 340° C., and is difficult to use as a hot melt molding material.

Further, in the literature, a polyarylate resin having a constituent unit derived from 9,9-bis(4-hydroxy-3-methylphenyl)fluorene is shown as a comparative example, and the polyarylate resin has a refractive index of 1.64, which is comparable to that of a general optical transparent resin, and has a relatively low glass transition temperature of 289° C., but as a result of examining the melt fluidity of the polyarylate resin, the inventors of the present application have found that the polyarylate resin has almost no melt fluidity even at 360° C., and is difficult to use as a hot melt molding material as in the case of the above-mentioned polyarylate resin.

In addition, it is known that among (meth)acrylate compounds, a difunctional (meth)acrylate compound derived from a bisphenol having a fluorene skeleton can form a resin exhibiting a high refractive index (e.g. PTD 4).

However, many of difunctional (meth)acrylate compounds derived from a bisphenol having a fluorene skeleton have a very high viscosity, or are in the form of a solid (powder), and therefore in production of a cured product, the viscosity should be reduced by forming the difunctional (meth)acrylate compound into a curable composition using a diluent such as an organic solvent or a monofunctional (meth)acrylate. However, many of difunctional (meth)acrylate compounds derived from a bisphenol having a fluorene skeleton have poor compatibility with the diluent, or a low solubility in the diluent, and therefore it is known that there arises the problem that preparation of a curable composition containing the (meth)acrylate compound in a high concentration is difficult, or the problem that a high refractive index to be developed by the (meth)acrylate compound is not sufficiently exhibited due to deflection of the refractive index caused by the diluent (e.g. PTD 5). In PTD 5, a cationically polymerizable liquid compound having an aromatic structure is added for solving the above-mentioned problem, but when a cationically polymerizable liquid compound is added, the refractive index tends to decrease as compared to a case where the cationically polymerizable liquid compound is not added.

In addition, a (meth)acrylate compound produced by ethylene-oxidating or propylene-oxidating the hydroxyl group of a bisphenol having a fluorene skeleton, and then (meth)acrylating the resultant group is known to be liquefied or have a reduced viscosity, or have improved compatibility or solubility with a diluent as compared to a (meth)acrylate compound produced without passing through such a step (e.g. PTD 6). However, even with the compound produced in this manner, the above-mentioned problem is not sufficiently solved in many cases, and further, there is the problem that the refractive index decreases as compared to a bisphenol compound produced without passing through the ethylene-oxidation or propylene-oxidation step, or the problem that the production cost and the number of steps for the resulting (meth)acrylate compound increase as the ethylene-oxidation or propylene-oxidation step is carried out.

On the other hand, epoxy resins generally form cured products excellent in mechanical properties, water resistance, chemical resistance, heat resistance, electrical properties and the like when cured with various curing agents. Thus, epoxy resins are used in a wide range of fields such as those of adhesives, coating materials, laminated sheets, molding materials, and casting materials. Among these epoxy resins, epoxy resins having a fluorene skeleton have a high refractive index, and are excellent in heat resistance etc., and these epoxy resins are being under extensive research and development for use in new fields such as those of sealing materials for semiconductor light emitting elements such as optical lenses and light emitting diodes (LEDs) in addition to the above-mentioned general fields where epoxy resins are used (e.g. PTD 7).

In particular, among epoxy resins having a fluorene skeleton, epoxy acrylate resins obtained by preparing an epoxy resin by epoxidizing a bisphenol represented by the formula (5), which has a phenyl group as a substituent, and further reacting the epoxy resin with acrylic acid are known to be used as raw materials for color filters that are suitably used for color liquid crystal displays etc. (e.g. PTD 8), or as films excellent in gas barrier property (e.g. PTD 9).

Thus, the epoxy resin having a fluorene skeleton is used not only as a sealing material obtained by curing the resin itself but also as a raw material for a resin obtained by reaction with other compounds such as acrylic acid and having a new structure, but there is the problem that the epoxy resin having a fluorene skeleton is poor in solubility in an organic solvent, and conditions for reaction with other compounds are limited.

CITATION LIST

Patent Document

PTD 1: Japanese Patent Laying-Open No. 2001-206863
PTD 2: Japanese Patent Laying-Open No. 2011-246583
PTD 3: Japanese Patent Laying-Open No. 2012-131865
PTD 4: Japanese Patent Laying-Open No. H04-325508
PTD 5: Japanese Patent Laying-Open No. 2009-235196
PTD 6: Japanese Patent Laying-Open No. 2010-18753
PTD 7: Japanese Patent Laying-Open No. S63-218725
PTD 8: Japanese Patent Laying-Open No. 2002-88136
PTD 9: Japanese Patent Laying-Open No. 2013-67146

SUMMARY OF INVENTION

Technical Problems

An object of the present invention is to provide a novel bisphenol which has a low melting point in view of processability and productivity, and can be used as a raw material of a resin exhibiting a refractive index, heat resistance and the like which are higher than or equal to the refractive index, heat resistance and the like of a bisphenol represented by the formula (5), and a method for producing the bisphenol.

Another object of the present invention is to provide a polyarylate resin which has a refractive index higher than or equal to that of a previously known transparent resin for an optical member, has improved heat resistance as compared to the transparent resin, and is excellent in fluidity during melting and solvent solubility, and a method for producing the polyarylate resin.

Still another object of the present invention is to provide a difunctional (meth)acrylate compound which has a low melt viscosity, is excellent in compatibility or solubility with a diluent such as an organic solvent or a monofunctional (meth)acrylate, and exhibits a refractive index higher than or equal to that of a difunctional (meth)acrylate compound derived from a previously known bisphenol compound having a fluorene skeleton, and a method for producing the difunctional (meth)acrylate compound.

Still another object of the present invention is to provide an epoxy resin which has higher solubility in an organic solvent and a lower melt viscosity as compared to a previously known epoxy resin having a fluorene skeleton, particularly an epoxy resin having a fluorene skeleton having a phenyl group as a substituent, and exhibits a refractive index and heat resistance which are higher than or equal to the refractive index and heat resistance of a previously known epoxy resin having a fluorene skeleton.

Solutions to Problems

The present inventors have extensively conducted studies for solving the above-mentioned problems, and resultantly found that a bisphenol represented by the following general formula (1) specifically has a low melting point; a polyarylate resin having a constituent unit derived from a bisphenol represented by the following general formula (1) exhibits a high refractive index, has heat resistance equal to that of a commonly used bisphenol A-type polyarylate resin, and is excellent in fluidity during melting and solvent solubility; a (meth)acrylate compound derived from a bisphenol represented by the following general formula (1) is excellent in compatibility or solubility with a diluent such as an organic solvent or a monofunctional (meth)acrylate, and has a low melt viscosity; and an epoxy resin including in the main chain a constituent unit derived from a bisphenol represented by the following general formula (1) is excellent in solubility in an organic solvent although the epoxy resin has a phenyl group as a substituent. Specifically, the present invention includes the following inventions:

[1]
a bisphenol represented by a general formula (1) below:

[Chemical Formula 2]

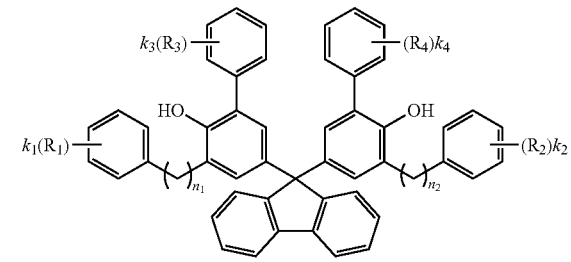

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different);

[2]

the bisphenol according to [1], in which in the general formula (1), $k_1$ to $k_4$ each represent 0, and $n_1$ and $n_2$ each represent 1;

[3]

a method for producing the bisphenol according to [1] or [2], the method including, in presence of an acid, reacting 9-fluorenone with a phenol compound represented by a general formula (2) below:

[Chemical Formula 3]

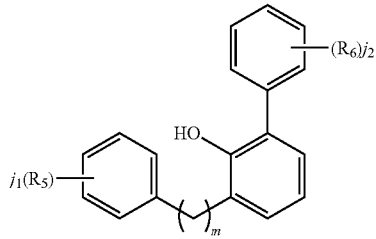

(2)

(where $R_5$ and $R_6$ are the same or different, and each represent an alkyl group, an aryl group or a halogen atom, m represents an integer of 1 to 4, and $j_1$ and $j_2$ are the same or different, and each represent 0 or an integer of 1 to 4; and when $j_1$ and/or $j_2$ are (is) 2 or more, corresponding $R_5$ and/or $R_6$ may be the same or different);

[4]

a polyarylate resin having a constituent unit derived from a bisphenol represented by a general formula (1) below:

[Chemical Formula 4]

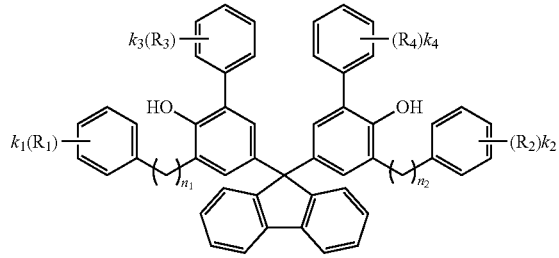

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different), and a constituent unit derived from an aromatic dicarboxylic acid;

[5]

the polyarylate resin according to [4], in which in the general formula (1), $k_1$ to $k_4$ each represent 0, and $n_1$ and $n_2$ each represent 1;

[6]

a method for producing the polyarylate resin according to [4] or [5], the method including polymerizing the bisphenol and the aromatic dicarboxylic acid or a derivative of the aromatic dicarboxylic acid;

[7]

a (meth)acrylate compound represented by a general formula (3) below:

[Chemical Formula 5]

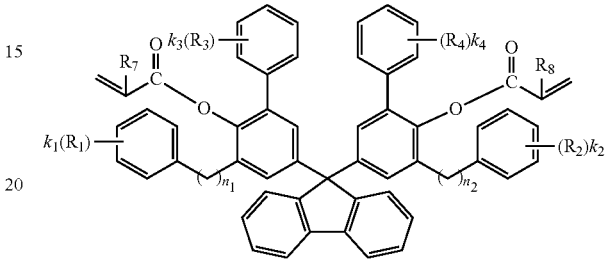

(3)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different; and $R_7$ and $R_8$ are the same or different, and each represent a hydrogen atom or a methyl group);

[8]

the (meth)acrylate compound according to [7], in which in the general formula (3), $k_1$ to $k_4$ each represent 0, and $n_1$ and $n_2$ each represent 1;

[9]

a method for producing the (meth)acrylate compound according to [7] or [8], the method including reacting a (meth)acrylic acid with a bisphenol represented by a general formula (1) below:

[Chemical Formula 6]

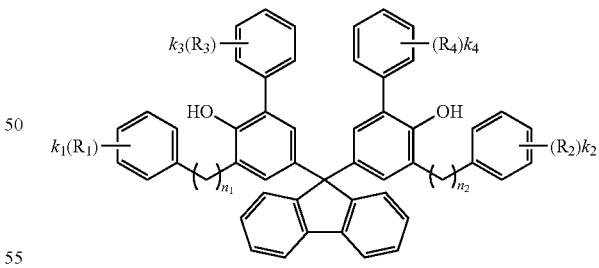

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different);

[10]

an epoxy resin including in a main chain a constituent unit derived from a bisphenol represented by a general formula (1) below:

[Chemical Formula 7]

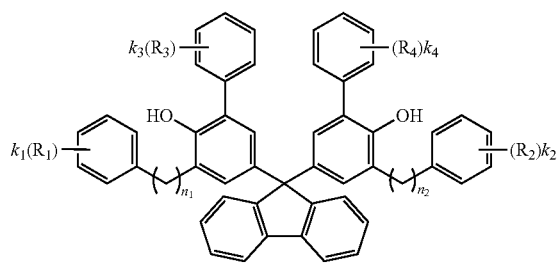

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different);

[11]
the epoxy resin according to [10], which is represented by a general formula (4) below:

[Chemical Formula 8]

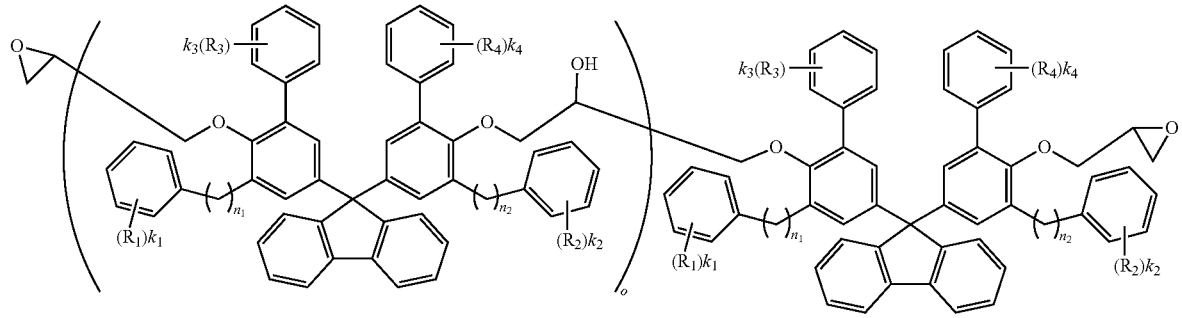

(4)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; when at least one of $k_1$ to $k_4$ is 2 or more, corresponding $R_1$ to $R_4$ may be the same or different; and p represents 0 or an integer of 1 or more);

[12]
the epoxy resin according to [11], in which in the general formula (4), $k_1$ to $k_4$ each represent 0, and $n_1$ and $n_2$ each represent 1;

[13]
a method for producing the epoxy resin according to any one of [10] to [12], the method including reacting the bisphenol with epihalohydrin;

[14]
a curable composition including the (meth)acrylate compound according to [7] or [8];

[15]
a cured product obtained by curing the curable composition according to [14];

[16]
a resin composition including the epoxy resin according to any one of [10] to [12];

[17]
a cured product obtained by curing the resin composition according to [16];

[18]
a molded product including at least one cured product or resin selected from the group consisting of the polyarylate resin according to [4] or [5], the cured product according to [15], and the cured product according to [17]; and

[19]
the molded product according to [18], in which the molded product is an optical member.

Advantageous Effects of Invention

In general, although the melting point of a bisphenol having a fluorene skeleton tends to increase as the number of phenyl groups increases, a bisphenol represented by the general formula (1) according to the present invention specifically has a low melting point, the refractive index of the bisphenol itself is high, and a 5% weight loss temperature which may be one index of heat resistance is high. Therefore, the bisphenol of the present invention can be suitably used as a monomer for a thermoplastic resin such as polycarbonate, polyester or polyester polycarbonate, particularly as a raw material (monomer) of a resin to be used for optical members (e.g. prism sheets, overcoating agents, hard coating agents, antireflection films or optical films, optical sheets, optical fibers, optical waveguides, holograms, films for liquid crystals, films for organic EL, various optical lenses and the like, which are used for liquid crystal display devices).

In addition, the polyarylate resin of the present invention which has a constituent unit derived from a bisphenol represented by the general formula (1), and a constituent unit derived from an aromatic dicarboxylic acid has a refractive index higher than or equal to that of a previously known resin to be used for optical members, has improved heat resistance as compared to the previously known resin, and is excellent in fluidity during melting and solvent solubility. Therefore, the polyarylate resin of the present invention can be suitably used for the above-mentioned optical members. In particular, the polyarylate resin of the present invention has higher heat resistance as compared to a previously known resin to be used for optical members, and therefore can be suitably used for devices that are exposed to harsh environments such as outdoor environments or in-vehicle environments, among the above-mentioned optical members.

In addition, the (meth)acrylate compound represented by the general formula (3) according to the present invention has a low melt viscosity, is excellent in compatibility or solubility with a diluent such as an organic solvent or a monofunctional (meth)acrylate, and exhibits a refractive index higher than or equal to that of a difunctional (meth) acrylate compound derived from a previously known bisphenol compound having a fluorene skeleton or a binaphthyl skeleton, which has been said to have a high refractive index.

Further, since the (meth)acrylate compound of the present invention has both excellent transparency and a low Abbe number, a curable composition containing the (meth) acrylate compound of the present invention in a high concentration can be obtained, and a cured product obtained by heat-curing or/and photocuring the curable composition can eliminate a chromatic aberration particularly when combined with a material having a high Abbe number. Therefore, the (meth)acrylate compound of the present invention can be suitably used as a raw material for the above-mentioned optical members in which the chromatic aberration causes a problem, and the refractive index is preferably high.

In addition, despite the epoxy resin of the present invention which has a bisphenol fluorene skeleton, the epoxy resin of the present invention which includes in the main chain a constituent unit derived from a bisphenol represented by the general formula (1) has an excellent solubility in an organic solvent and, a low melt viscosity, besides the epoxy resin exhibits a refractive index and heat resistance which are higher than or equal to the refractive index and heat resistance of a previously known epoxy resin having a bisphenol fluorene skeleton.

DESCRIPTION OF EMBODIMENTS

<Bisphenol>

Figure 1:
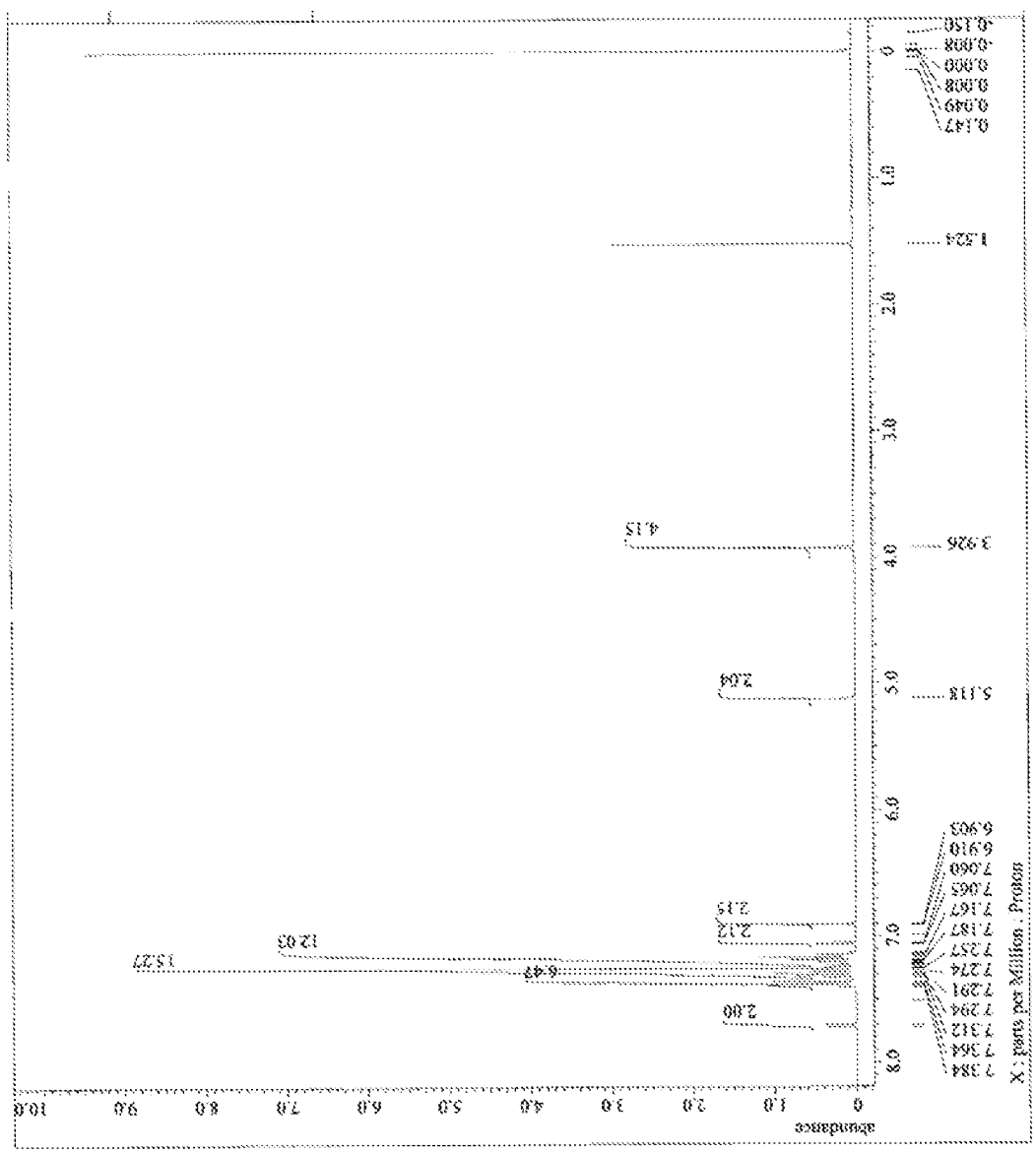
FIG. 1 shows a $^1$H-NMR chart of a bisphenol obtained in Example 1 and represented by the following formula (1-1).

A bisphenol of the present invention is represented by the general formula (1) (hereinafter, sometimes referred to as a bisphenol of the present invention). Examples of the alkyl group in the substituents ($R_1$ to $R_4$) in the general formula (1) include optionally branched alkyl groups such as a methyl group, an ethyl group, a propyl group and an isopropyl group, and cyclic alkyl groups such as a cyclopentyl group and a cyclohexyl group. Examples of the aryl group include aromatic groups optionally having a substituent, such as a phenyl group and a tolyl group. Examples of the halogen atom include a fluorine atom, a chlorine atom, a bromine atom and an iodine atom. Among these substituents shown as examples, optionally branched alkyl groups having 1 to 4 carbon atoms are preferable from the viewpoint of availability of a raw material that is a phenol compound represented by the general formula (2).

$k_1$ to $k_4$ representing the number of substituents ($R_1$ to $R_4$) are the same or different, and each represent 0 or an integer of 1 to 4, preferably 0 or an integer of 1 to 2, more preferably 0 or 1 from the viewpoint of availability of a raw material that is a phenol compound represented by the general formula (2). When at least one of $k_1$ to $k_4$ is 2 or more, the corresponding substituents may be the same or different.

$n_1$ and $n_2$ representing the number of methylene groups connecting a phenyl group having a hydroxyl group and the other phenyl group are the same or different, and each represent an integer of 1 to 4, preferably 1 or 2, more preferably 1 from the viewpoint of availability of a raw material that is a phenol compound represented by the general formula (2).

The bisphenol represented by the general formula (1) according to the present invention has a melting point of normally 250° C. or lower, particularly 230° C. or lower, more particularly 200° C. or lower. Therefore, when the bisphenol represented by the general formula (1) according to the present invention is used in a method requiring a reaction temperature higher than or equal to the melting point of a raw material on a temporary basis as in a melt polymerization method, it is possible to reduce the reaction temperature or shorten the time during which the raw material is exposed to a high temperature, and therefore coloring of the resulting resin can be avoided.

The bisphenol represented by the general formula (1) according to the present invention has a refractive index of normally 1.63 or more, particularly 1.65 or more, more particularly 1.66 or more as measured under the later-described conditions. In addition, since the 5% weight loss temperature is normally 300° C. or higher, particularly 320° C. or higher, the bisphenol can be used as a raw material for a resin exhibiting a high refractive index and high heat resistance.

<Method for Producing Bisphenol>

The bisphenol represented by the general formula (1) according to the present invention can be produced by reacting a phenol compound represented by the above general formula (2) with 9-fluorenone (hereinafter, sometimes referred to as fluorenone) in the presence of an acid (hereinafter, the reaction is sometimes referred to as a "bisphenol formation reaction"). Hereinafter, the bisphenol formation reaction will be described in detail.

The phenol compound represented by the general formula (2) is a generally available compound, and a commercially available product may be used, or one having a desired structure can be produced by a known method, e.g. a method as described in Journal of Organic Chemistry 1970, 35(1), 57-62. Examples of the alkyl group in the substituents ($R_5$ and $R_6$) in the general formula (2) include optionally branched alkyl groups such as a methyl group, an ethyl group, a propyl group and an isopropyl group, and cyclic alkyl groups such as a cyclopentyl group and a cyclohexyl group. Examples of the aryl group include aromatic groups optionally having a substituent, such as a phenyl group and a tolyl group. Examples of the halogen atom include a fluorine atom, a chlorine atom, a bromine atom and an iodine atom. Among these substituents shown as examples, optionally branched alkyl groups having 1 to 4 carbon atoms are preferable from the viewpoint of ease of producing a phenol compound represented by the general formula (2).

$j_1$ and $j_2$ representing the number of substituents ($R_5$ and $R_6$) are the same or different, and each represent 0 or an integer of 1 to 4, preferably 0 or an integer of 1 to 2, more preferably 0 or 1 from the viewpoint of ease of producing a phenol compound represented by the general formula (2). When each of $j_1$ and $j_2$ is 2 or more, the corresponding substituents may be the same or different.

m's representing the number of methylene groups connecting a phenyl group having a hydroxyl group and the other phenyl group are the same or different, and each represent an integer of 1 to 4, preferably 1 or 2, more preferably 1 from the viewpoint of ease of producing a phenol compound represented by the general formula (2).

The use amount of the phenol compound represented by the general formula (2) is normally 2 to 5 mol, preferably 2 to 3 mol based on 1 mole of fluorenone from the viewpoint of economically producing a bisphenol represented by the general formula (1). Two or more phenol compounds represented by the general formula (2) may be mixed and used as necessary. When two or more phenol compounds are mixed and used, an asymmetric bisphenol represented by the general formula (1) can be produced.

As the acid to be used in the bisphenol formation reaction, for example, various acids such as inorganic acids and organic acids can be used. Specific examples thereof include inorganic acids such as sulfuric acid, hydrogen chloride, hydrochloric acid, phosphoric acid, heteropolyacid, zeolite and clay minerals, and organic acids such as methanesulfonic acid, trifluoromethanesulfonic acid, para-toluenesulfonic acid and ion-exchange resins. Among them, hydrochloric acid or para-toluenesulfonic acid is preferably used from the viewpoint of availability and handling property. The use amount of the acid is usually 0.1 to 5.0 mol based on 1 mole of fluorenone, preferably 0.5 to 1.0 mol based on 1 mole of fluorenone from the viewpoint of obtaining a sufficient reaction rate and ease of post-treatment. One of these acids may be used alone, or two or more of these acids may be mixed and used as necessary.

At the time of carrying out the bisphenol formation reaction, it is preferable that a sulfur-containing compound coexist from the viewpoint of improving the reaction rate. Examples of the usable sulfur-containing compound include mercaptocarboxylic acids, alkyl mercaptans, aralkyl mercaptans and salts thereof. Specific examples thereof include $C_{1-16}$ alkyl mercaptans such as thioacetic acid, β-mercaptopropionic acid, α-mercaptopropionic acid, thioglycolic acid, thio-oxalic acid, mercaptosuccinic acid, mercaptobenzoic acid, n-butylmercaptan and dodecylmercaptan. Among these sulfur-containing compounds, dodecyl mercaptan is suitably used because it has a favorable industrial handling property. When such a sulfur-containing compound is used, the use amount of the sulfur-containing compound is normally 0.01 to 1.0 parts by weight based on 1 part by weight of fluorenone, preferably 0.01 to 0.50 parts by weight based on 1 part by weight of fluorenone from the viewpoint of obtaining a sufficient reaction rate and ease of post-treatment. One of these sulfur-containing compounds may be used alone, or two or more of these sulfur-containing compounds may be mixed and used as necessary.

At the time of carrying out the bisphenol formation reaction, the reaction may be carried out in the presence of a solvent as necessary. Examples of the usable solvent include aliphatic hydrocarbons, aromatic hydrocarbons, ethers and halogenated hydrocarbons. Examples of the usable solvent include aliphatic hydrocarbons such as alkanes such as hexane, heptane, octane and decane; aromatic hydrocarbons such as benzene, toluene, xylene and ethylbenzene; ethers such as dialkyl ethers such as diethyl ether, and cyclic ethers such as tetrahydrofuran and dioxane; and halogenated hydrocarbons such as aliphatic halogenated hydrocarbons such as methylene chloride, chloroform and carbon tetrachloride, and aromatic halogenated hydrocarbons such as chlorobenzene and dichlorobenzene. Among these solvents, aromatic hydrocarbons such as toluene and xylene are suitably used from the viewpoint of availability and handling property. When such a solvent is used, the use amount of the solvent is normally 0.1 to 10 parts by weight based on 1 part by weight of fluorenone, preferably 0.5 to 5.0 parts by weight based on 1 part by weight of fluorenone from the viewpoint of obtaining a sufficient reaction rate and economic efficiency. One of these solvents may be used alone, or two or more of these solvents may be mixed and used as necessary.

The bisphenol formation reaction is carried out by, for example, adding fluorenone, a phenol compound represented by the general formula (2), an acid, and a sulfur-containing compound and a solvent as necessary in a reactor, and stirring the mixture at an internal temperature of normally 50 to 200° C., preferably 80 to 140° C. In addition, from the viewpoint of obtaining a sufficient reaction rate, the reaction may be carried out while water is removed under reflux at normal pressure or reduced pressure as necessary.

After the bisphenol formation reaction, the resulting reaction liquid can be subjected to a normal method such as neutralization, washing with water, concentration, crystallization or filtration as necessary to extract a bisphenol represented by the general formula (1). The resulting bisphenol represented by the general formula (1) can also be purified by a conventional method such as recrystallization, distillation, adsorption, column chromatography or the like. As necessary, the resulting reaction liquid may be used as such for production of a polyarylate resin, an acrylate compound or an epoxy resin as described later.

<Polyarylate Resin>

A polyarylate resin of the present invention is a resin having a constituent unit derived from a bisphenol represented by the general formula (1) and a constituent unit derived from an aromatic dicarboxylic acid (hereinafter, referred to as a polyarylate resin of the present invention).

The polyarylate resin of the present invention may have other bisphenol-derived constituent units besides the constituent unit derived from a bisphenol represented by the general formula (1) as long as the effect of the present invention is not impaired. Examples of other bisphenols include bisphenol A, tetramethyl bisphenol A, 1,1-bis(4-hydroxyphenyl)-1-phenylethane, 1,1-bis(4-hydroxyphenyl)cyclohexane, 1,1-bis(4-hydroxyphenyl)ethane, 1,1-bis(3,5-dimethyl-4-hydroxyphenyl)ethane, 1,1-bis(3-methyl-4-hydroxyphenyl)ethane, bis(4-hydroxyphenyl)methane, bis(3,5-dimethyl-4-hydroxyphenyl)methane, bis(3-methyl-4- hydroxyphenyl)methane, 1,1-bis(3,5-dimethyl-4-hydroxyphenyl)cyclohexane, 9,9-bis(4-hydroxyphenyl)fluorene, 9,9-bis(3-methyl-4-hydroxyphenyl)fluorene, 9,9-bis(2-hydroxy-4-ethylphenyl)fluorene, 9,9-bis(4-hydroxy-3,5-dimethylphenyl)fluorene, spiro[fluorene-9,9'-(2',7'-dihydroxyxanthene)], and binaphthols such as 1,1'-bi-2-naphthol.

When the polyarylate resin has constituent units derived from other bisphenols, the ratio of the constituent unit derived from a bisphenol represented by the general formula (1) is 90 mol % or more, preferably 95 mol % or more, more preferably 99 mol % or more based on the total amount of bisphenol-derived constituent units.

Examples of the aromatic dicarboxylic acid that forms the polyarylate resin of the present invention include phthalic acids such as terephthalic acid, isophthalic acid and orthophthalic acid; phthalic acid derivatives such as terephthalic acid and isophthalic acid substituted with one or two alkyl groups selected from the group consisting of a methyl group, an ethyl group, a n-propyl group, an isopropyl group, a n-butyl group, an isobutyl group, a sec-butyl group and a tert-butyl group; biphenyldicarboxylic acids such as 4,4'-biphenyldicarboxylic acid [BPDC] and 2,2'-biphenyldicarboxylic acid; naphthalenedicarboxylic acids such as 1,5-naphthalenedicarboxylic acid and 2,6-naphthalenedicarboxylic acid; and diphenyl ether dicarboxylic acids such as diphenyl ether-2,2'-dicarboxylic acid, diphenyl ether-2,3'-dicarboxylic acid, diphenyl ether-2,4'-dicarboxylic acid, diphenyl ether-3,3'-dicarboxylic acid, diphenyl ether-3,4'-dicarboxylic acid and diphenyl ether-4,4'-dicarboxylic acid. One of these aromatic dicarboxylic acids may be used alone, or two or more of these aromatic dicarboxylic acids may be combined and used. Among these aromatic dicarboxylic acids, phthalic acids (terephthalic acid, isophthalic acid and the like), naphthalene dicarboxylic acids and biphenyl dicarboxylic acids are suitably used.

In the present invention, the polyarylate resin may contain other component-derived constituent units besides the constituent unit derived from a bisphenol represented by the general formula (1) and the constituent unit derived from an aromatic dicarboxylic acid as long as the effect of the present invention is not impaired. Examples of other components that may be contained include aliphatic diols, cycloaliphatic diols, aliphatic dicarboxylic acids and cycloaliphatic dicarboxylic acids, and examples of the aliphatic diol include ethylene glycol and propylene glycol. Examples of the cycloaliphatic diol include 1,4-cyclohexanediol, 1,3-cyclohexanediol and 1,2-cyclohexanediol. Examples of the aliphatic dicarboxylic acid include adipic acid and sebacic acid. Examples of the cycloaliphatic dicarboxylic acid include 1,4-cyclohexanedicarboxylic acid, 1,3-cyclohexanedicarboxylic acid and 1,2-cyclohexanedicarboxylic acid.

From the viewpoint of exhibiting properties such as a high refractive index without impairing handling property during production, the weight average molecular weight (Mw) of the polyarylate resin of the present invention can be selected from a range of about 5000 to 200000, and is, for example, 6000 to 150000, particularly 8000 to 120000, more particularly 10000 to 100000.

The glass transition temperature of the polyarylate resin of the present invention is preferably 150° C. or higher from the viewpoint of heat resistance, and the upper limit of the glass transition temperature is, for example, 230° C. or lower, preferably 210° C. or lower, more preferably 200° C. or lower from the viewpoint of molding processability. Thus, the polyarylate resin of the present invention has both heat resistance and molding processability, and therefore can be suitably used as a hot melt molding material that is required to have heat resistance.

The refractive index of the polyarylate resin of the present invention is, for example, 1.62 or more, particularly 1.64 or more, at a temperature of 20° C. and a wavelength of 589 nm. Thus, the polyarylate resin of the present invention can exhibit a refractive index higher than or equal to the refractive index of a high-refractive-index polycarbonate or the like which is used for optical members.

For the fluidity of the polyarylate resin of the present invention, the MFR (melt flow rate) is 10 g/10 min or more at 285° C. and 100 g/10 min or more at 360° C., preferably 20 g/10 min or more at 285° C. and 500 g/10 min or more at 360° C., in a fluidity test conducted by a method as described later. Thus, the polyarylate resin of the present invention is excellent in fluidity during melting, and therefore can be molded by hot melt molding such as injection molding or extrusion molding as in the case of a previously known thermoplastic resin, so that a precise molded product can be produced inexpensively.

The polyarylate resin of the present invention has a rigid skeleton, i.e. the constituent unit derived from a bisphenol represented by the general formula (1) and the constituent unit derived from an aromatic dicarboxylic acid, but is excellent in solvent solubility. For example, the polyarylate resin of the present invention is soluble in common solvents such as ethers (e.g. tetrahydrofuran), hydrocarbons (aromatic hydrocarbons such as toluene), amides (e.g. N,N-dimethylformamide), ketones (e.g. cyclic ketones such as cyclopentanone and cyclohexanone) and halogenated hydrocarbons (e.g. methylene chloride and chloroform). Thus, the polyarylate resin of the present invention can be used not only in hot melt molding, but also in molding (film formation) using a solvent, such as solution casting method.

<Method for Producing Polyarylate Resin>

The polyarylate resin of the present invention can be produced by polymerizing a bisphenol represented by the general formula (1) and an aromatic dicarboxylic acid or a derivative thereof.

The use amount of the aromatic dicarboxylic acid is normally 0.9 to 2.0 mol, preferably 1.0 to 1.2 mol based on 1 mole of a bisphenol represented by the general formula (1). In addition, in production of the polyarylate resin of the present invention, a derivative of an aromatic dicarboxylic acid can be used besides the aromatic dicarboxylic acid. Examples of the usable derivative of an aromatic dicarboxylic acid include esters {e.g. alkyl esters [e.g. lower alkyl esters such as methyl esters and ethyl esters (e.g. $C_{1-4}$ alkyl esters, particularly $C_{1-2}$ alkyl esters)] and the like}, acid halides (acid chlorides and the like) and acid anhydrides of aromatic dicarboxylic acids. The derivatives of aromatic dicarboxylic acids may be monoesters (half esters) or diesters, or monoacid halides or dihalides.

Examples of the polymerization method usable for producing the polyarylate resin of the present invention include an interfacial polymerization method, a solution polymerization method and a melt polymerization method, with the interfacial polymerization method being preferable. With the interfacial polymerization method, the reaction rate is higher as compared to the solution polymerization method and the melt polymerization method, and a high-molecular-weight polyarylate resin can be easily obtained. The interfacial polymerization method is a polymerization method with which the molecular weight of the resulting polyarylate resin is easily controlled, and excellent low-impurity property and transparency can be imparted. The interfacial polymerization method is generally carried out in the following manner: an alkali suspension liquid (aqueous phase) obtained by mixing an alkali aqueous solution with a bisphenol represented by the general formula (1) and an organic phase obtained by mixing a water-insoluble organic solvent with a dicarboxylic acid dihalide being a derivative of an aromatic dicarboxylic acid are mixed each other in the presence of a catalyst. A specific method for carrying out the interfacial polymerization method is described in, for example, W. M. EARECKSON, J. Poly. Sci. XL 399 (1959), JP-B-S40-1959 or the like. Hereinafter, the interfacial polymerization method in the present invention will be described in detail.

As the aqueous phase, a bisphenol represented by the general formula (1) is mixed with an alkali aqueous solution, and a polymerization catalyst, and an end-capping agent as necessary are then added. Separately, an organic phase is prepared in the following manner: an aromatic dicarboxylic acid dihalide being a raw material for introducing a constituent unit derived from an aromatic dicarboxylic acid is dissolved in an organic solvent for preparing an organic phase as described later. Thereafter, the aqueous phase is mixed with the organic phase, and an interfacial polymerization reaction is carried out to generate a high-molecular-weight polyarylate resin in the organic layer. Thereafter, the organic layer containing the polyarylate resin is washed with pure water, ion-exchanged water or the like, and then added dropwise to a poor solvent to precipitate the polyarylate resin, and the precipitated resin is separated by filtration, or the organic solvent is distilled off to obtain the polyarylate resin.

Examples of the alkali for preparing the alkali aqueous solution include sodium hydroxide and potassium hydroxide, and sodium hydroxide is preferable from the viewpoint of an economic advantage and ease of waste liquid treatment. The use amount of the alkali is 2.0 to 8.0 mol, preferably 3.0 to 5.0 mol based on 1 mole of a bisphenol represented by the general formula (1).

Examples of the polymerization catalyst include tertiary amines such as trimethylamine, triethylamine, tri-n-butylamine, trihexylamine, tridodecylamine, N, N-dimethylcyclohexylamine, pyridine, quinoline and dimethylaniline; quaternary ammonium salts such as trimethylbenzylammonium halides, tributylbenzylammonium halides, triethylbenzylammonium halides, tributylbenzylphosphonium halides and tetrabutylammonium halides; and quaternary phosphonium salts such as trimethylbenzylphosphonium halides, tributylbenzylphosphonium halides, triethylbenzylphosphonium halides, tetrabutylphosphonium halides, triphenylbenzylphosphonium halides and tetraphenylphosphonium halides. Among them, tributylbenzylammonium halides, tetrabutylammonium halides and tetrabutylphosphonium halides are preferable from the viewpoint of increasing the reaction rate and minimizing the hydrolysis of the aromatic dicarboxylic acid halide. The use amount of the polymerization catalyst is 0.0001 to 0.05 mol, preferably 0.001 to 0.01 mol based on 1 mole of the bisphenol represented by the general formula (1).

Examples of the end-capping agent include monohydric phenols, monovalent acid chlorides, monohydric alcohols and monovalent carboxylic acids. Examples of the monohydric phenol include phenol, o-cresol, m-cresol, p-cresol, p-tert-butylphenol, o-phenylphenol, m-phenylphenol, p-phenylphenol, o-methoxyphenol, m-methoxyphenol, p-methoxyphenol, 2,3,6-trimethylphenol, 2,3-xylenol, 2,4-xylenol, 2,5-xylenol, 2,6-xylenol, 3,4-xylenol, 3,5-xylenol, 2-phenyl-2-(4-hydroxyphenyl)propane, 2-phenyl-2-(2-hydroxyphenyl)propane and 2-phenyl-2-(3-hydroxyphenyl) propane. Examples of the monovalent acid chloride include benzoyl chloride, benzoic acid chloride, methanesulfonyl chloride and phenyl chloroformate. Examples of the monohydric alcohol include methanol, ethanol, n-propanol, isopropanol, n-butanol, 2-butanol, pentanol, hexanol, dodecyl alcohol, stearyl alcohol, benzyl alcohol and phenethyl alcohol. Examples of the monovalent carboxylic acid include acetic acid, propionic acid, octanoic acid, cyclohexanecarboxylic acid, benzoic acid, toluic acid, phenylacetic acid, p-tert-butylbenzoic acid and p-methoxyphenylacetic acid. Among these end-capping materials, p-tert-butylphenol is preferable because it has high thermal stability. The use amount of the end-capping agent is 0.01 to 0.2 mol, preferably 0.03 to 0.1 mol based on 1 mole of a bisphenol represented by the general formula (1).

The solvent for preparing an organic phase may be a solvent which is not compatible with water and in which the polyarylate resin is soluble. Examples of the solvent include chlorine-based solvents such as methylene chloride, 1,2-dichloroethane, chloroform, carbon tetrachloride, chlorobenzene, 1,1,2,2-tetrachloroethane, 1,1,1-trichloroethane, o-dichlorobenzene and m-dichlorobenzene; aromatic hydrocarbon-based solvents such as toluene, benzene and xylene; and ether-based solvents such as tetrahydrofuran. Among them, methylene chloride is preferable because it is nonflammable, and has favorable handling property. The use amount of the solvent is 3 to 30 parts by weight, preferably 10 to 20 parts by weight based on 1 part by weight of a bisphenol represented by the general formula (1).

The temperature at which interfacial polymerization is performed is normally 0 to 50° C., preferably 10 to 40° C., more preferably 20 to 30° C. When the temperature is higher than or equal to 0° C., a sufficient reaction rate can be obtained, and when the temperature is lower than or equal to 50° C., production of impurities can be suppressed to obtain the polyarylate resin of the present invention, which has a higher purity.

After completion of interfacial polymerization, the salt is normally removed by separating and removing the aqueous phase. Thereafter, neutralization is carried out with an acid such as acetic acid, hydrochloric acid or oxalic acid so that the pH is 4.0 to 8.0. After neutralization, washing with water and removal of liquids are repeated to obtain a solution containing a polyarylate resin. In addition, a filtration operation may be added before a solution containing a polyarylate resin is obtained.

The resulting solution containing a polyarylate resin is added dropwise to a poor solvent to precipitate the polyarylate resin, and the precipitated resin is separated by filtration, or the organic solvent is distilled off from the solution to obtain the polyarylate resin.

<(Meth)Acrylate Compound>

A (meth)acrylate compound of the present invention is a (meth)acrylate compound having a structure represented by the general formula (3) (hereinafter, sometimes referred to as a (meth)acrylate compound of the present invention).

Examples of the alkyl group in the substituents ($R_1$ to $R_4$) in the general formula (3) include optionally branched alkyl groups such as a methyl group, an ethyl group, a propyl group and an isopropyl group, and cyclic alkyl groups such as a cyclopentyl group and a cyclohexyl group. Examples of the aryl group include aromatic groups optionally having a substituent, such as a phenyl group and a tolyl group. Examples of the halogen atom include a fluorine atom, a chlorine atom, a bromine atom and an iodine atom. Among these substituents shown as examples, optionally branched alkyl groups having 1 to 4 carbon atoms are preferable for the same reason as described above for the preferred aspect of a bisphenol represented by the general formula (1).

$k_1$ to $k_4$ representing the number of substituents ($R_1$ to $R_4$) are the same or different, and each represent 0 or an integer of 1 to 4, preferably 0 or an integer of 1 to 2, more preferably 0 or 1 for the same reason as described above for the preferred aspect of a bisphenol represented by the general formula (1). When at least one of $k_1$ to $k_4$ is 2 or more, the corresponding substituents may be the same or different.

$n_1$ and $n_2$ representing the number of methylene groups connecting a phenyl group having a (meth)acryloyl group and the other phenyl group are the same or different, and each represent an integer of 1 to 4, preferably 1 or 2, more preferably 1 for the same reason as described above for the preferred aspect of a bisphenol represented by the general formula (1).

The (meth)acrylate compound of the present invention may contain as impurities a monoacrylate as an intermediate, a bisphenol represented by the general formula (1) as an unreacted raw material, and so on as long as properties as the (meth)acrylate compound of the present invention are not impaired.

The (meth)acrylate compound of the present invention is excellent in compatibility or solubility with a diluent such as an organic solvent or a monofunctional (meth)acrylate. In addition, since the (meth)acrylate compound has a low melt viscosity, it has an excellent handling property and it is possible to prepare a curable composition which contains the (meth)acrylate compound of the present invention in a high concentration. Therefore, it is possible to easily obtain a curable composition capable of sufficiently exhibiting the properties of the (meth)acrylate compound of the present invention as described later, and a cured product obtained by curing the curable composition.

The (meth)acrylate compound of the present invention has a refractive index of normally 1.60 or more, particularly 1.62 or more, more particularly 1.63 or more as measured under conditions as described later. In addition, the (meth)acrylate compound has an Abbe number of 22 or less, particularly 20 or less, and can eliminate a chromatic aberration particularly when combined with a material having a high Abbe number. Therefore, the (meth)acrylate compound can be suitably used for various optical materials in which the chromatic aberration causes a problem, and the refractive index is preferably high.

<Method for Producing (Meth)Acrylate Compound>

The (meth)acrylate compound of the present invention is obtained by reacting a bisphenol represented by the general formula (1) and a (meth)acrylic acid (hereinafter, sometimes referred to as an acrylate formation reaction).

Examples of the (meth)acrylic acid to be used in the acrylate formation reaction include (meth)acrylic acids, (meth)acrylic acid lower alkyl esters (e.g. $C_{1-4}$ alkyl (meth)acrylates such as methyl (meth)acrylate, ethyl (meth)acrylate and butyl (meth)acrylate), (meth)acrylic acid halides (e.g. (meth)acrylic acid chloride), and (meth)acrylic acid anhydrides.

The use amount of the (meth)acrylic acid is normally 2 to 20 mol, preferably 2.2 to 10 mol, more preferably 2.5 to 5 mol based on 1 mole of a bisphenol represented by the general formula (1).

In the acrylate formation reaction, an acid, a base and the like may be appropriately used.

As the acid that can be used in the acrylate formation reaction, for example, various acids such as inorganic acids and organic acids can be used. Specific examples thereof include inorganic acids such as sulfuric acid, hydrogen chloride, hydrochloric acid, phosphoric acid, heteropolyacid, zeolite and clay minerals, and organic acids such as methanesulfonic acid, trifluoromethanesulfonic acid, para-toluenesulfonic acid and ion-exchange resins. Among these acids, hydrochloric acid and para-toluenesulfonic acid are suitably used. One of these acids may be used alone, or two or more of these acids may be mixed and used as necessary.

As a base that can be used in the acrylate formation reaction, for example, an inorganic base or an organic base can be used, and examples of the inorganic base include metal carbonates (e.g. alkali metal carbonates or alkaline earth metal carbonates such as sodium carbonate, and alkali metal hydrogencarbonates or alkaline earth metal hydrogencarbonates such as sodium hydrogencarbonate), metal carboxylates (e.g. alkali metal acetates or alkaline earth metal acetates such as sodium acetate and calcium acetate), and metal hydroxides (alkali metal hydroxides such as sodium hydroxide and alkaline earth metal hydroxides such as calcium hydroxide). Examples of the organic base include amines [e.g. tertiary amines (trialkylamines such as triethylamine, triisopropylamine and tributylamine, aromatic tertiary amines such as N,N-dimethylaniline, and heterocyclic tertiary amines such as pyridine)]. Among these bases, triethylamine is suitably used. One of these bases may be used alone, or two or more of these bases may be mixed and used as necessary.

The use amount of the acid, base or the like is, for example, 0.01 to 10 mol, preferably 0.05 to 5 mol, more preferably 0.1 to 3 mol based on 1 mole of a bisphenol represented by the general formula (1).

In addition, the acrylate formation reaction may be carried out in the presence of a polymerization inhibitor (thermal polymerization inhibitor) as necessary. Examples of the polymerization inhibitor include hydroquinones (e.g. hydroquinone; hydroquinone monoalkyl ethers such as hydroquinone monomethyl ether (methoquinone)), catechols (e.g. alkyl catechols such as t-butyl catechol), amines (e.g. diphenylamine), 2,2-diphenyl-1-picrylhydrazyl, and 4-hydroxy-2,2,6,6-tetramethylpiperazine-1-oxyl. One of the polymerization inhibitors may be used alone, or two or more of these polymerization inhibitors may be mixed and used as necessary.

The use amount of the polymerization inhibitor is, for example, 0.1 to 10 parts by weight, preferably 0.3 to 8 parts by weight, more preferably 0.5 to 5 parts by weight based on 100 parts by weight of the (meth)acrylic acid.

The acrylate formation reaction may be carried out without using a solvent, or carried out with an organic solvent. Examples of the organic solvent that can be used in combination include hydrocarbons, halogenated hydrocarbons, ethers, ketones and nitriles. Specific examples of the hydrocarbon include aliphatic hydrocarbons such as hexane, heptane and octane, and aromatic hydrocarbons such as benzene, toluene and xylene. Examples of the halogenated hydrocarbon include aliphatic halogenated hydrocarbons such as methylene chloride, chloroform and carbon tetrachloride, and aromatic halogenated hydrocarbons such as chlorobenzene and dichlorobenzene. Examples of the ether include dialkyl ethers such as diethyl ether, cyclic ethers such as tetrahydrofuran and dioxane, and anisole. Examples of the ketone include dialkyl ketones such as acetone and methyl ethyl ketone. Examples of the nitrile include acetonitrile, propionitrile and benzonitrile. One of these organic solvents may be used alone, or two or more of these organic solvents may be mixed and used as necessary. When the acid, base or the like is liquid, the acid, base or the like can also be used as a solvent.

When an organic solvent is used in combination, the use amount of the organic solvent is, for example, 0.5 to 20 parts by weight, preferably 1 to 10 parts by weight based on 1 part by weight of a bisphenol represented by the general formula (1).

The acrylate formation reaction is normally carried out at −20 to 80° C., preferably at 0 to 40° C. In addition, the acrylate formation reaction may be carried out while water and alcohols, which are by-products, are removed. The acrylate formation reaction can also be carried out under pressure or under reduced pressure.

After completion of the acrylate formation reaction, the later-described curable composition may be formed directly from the resulting reaction liquid without extracting a (meth)acrylate compound represented by the general formula (3). In addition, the curable composition may be formed after the (meth)acrylate compound represented by the general formula (3) is extracted by a normal method such as neutralization, washing with water, concentration, crystallization or filtration as necessary. Further, a curable composition may be formed after the temporarily extracted (meth)acrylate compound represented by the general formula (3) is purified by a conventional method such as recrystallization, distillation, adsorption or column chromatography.

<Curable Composition Containing (Meth)Acrylate Compound>

The curable composition containing a (meth)acrylate compound represented by the general formula (3) according to the present invention (hereinafter, sometimes referred to as the curable composition of the present invention) may contain other polyfunctional (meth)acrylates, a polymerization initiator, a diluent and so on in addition to the (meth)acrylate compound represented by the general formula (3). Since the (meth)acrylate compound represented by the general formula (3) has a low melt viscosity, only the (meth)acrylate compound represented by the general formula (3) can be used as a curable composition, and cured to obtain a cured product.

Examples of other polyfunctional (meth)acrylates that may be contained in the curable composition of the present invention include difunctional (meth)acrylates {e.g. alkylene glycol di(meth)acrylates [e.g. $C_{2-10}$ alkylene glycol di(meth)acrylates such as ethylene glycol di(meth)acrylate, propylene glycol di(meth)acrylate and 1,4-butanediol di(meth)acrylate], polyalkylene glycol di(meth)acrylates [$C_{2-4}$ alkylene glycol di(meth)acrylates such as di-to-tetraethylene glycol di(meth)acrylate, polyethylene glycol di(meth)acrylate, di-to-tetrapropylene glycol di(meth)acrylate and polytetramethylene glycol di(meth)acrylate], di(meth)acrylate of bisphenol A (or $C_{2-3}$ alkylene oxide adduct thereof); tri-or-more-functional polyfunctional (meth)acrylates [e.g. tri- or tetra(meth)acrylates of tri- or tetraols such as glycerin tri(meth)acrylate, trimethylolpropane tri(meth)acrylate, tris(hydroxyethyl)isocyanurate tri(meth)acrylate, pentaerythritol tri- or tetra(meth)acrylate; ditrimethylolpropane tetra(meth)acrylate; and dipentaerythritol tetra-to-hexa(meth)acrylate], urethane (meth)acrylate, epoxy (meth)acrylate, polyester (meth)acrylate; and polyfunctional (meth)acrylate having a fluorene skeleton {9,9-bis((meth)acryloyloxyphenyl)fluorenes such as 9,9-bis(4-(meth)acryloyloxyphenyl)fluorene and 9,9-bis(4-(meth)acryloyloxy-3-methylphenyl)fluorene; and 9,9-bis[(meth)acryloyloxy(poly)ethoxyphenyl]fluorenes such as 9,9-bis[4-(2-(meth)acryloyloxyethoxy)-3-methylphenyl]fluorene}. One of these other polyfunctional (meth)acrylates may be used alone, or two or more of these polyfunctional (meth)acrylates may be mixed and used as necessary.

When other polyfunctional (meth)acrylates are used in combination, the use amount thereof is, for example, 1 to 300 parts by weight, preferably 2 to 200 parts by weight, more preferably 5 to 100 parts by weight based on 100 parts by weight of a (meth)acrylate compound represented by the general formula (3).

Examples of the polymerization initiator that can be contained in the curable composition of the present invention include thermal polymerization initiators and photopolymerization initiators, and the thermal polymerization initiator and the photopolymerization initiator can be used in combination as necessary. Examples of the thermal polymerization initiator include dialkyl peroxides (e.g. di-t-butyl peroxide and dicumyl peroxide); diacyl peroxides [dialkanoyl peroxide (e.g. lauroyl peroxide) and diaroyl peroxide (e.g. benzoyl peroxide)]; peracid esters (e.g. t-butyl peracetate); organic peroxides such as ketone peroxides, peroxycarbonates and peroxyketals; and azo compounds such as azonitrile compounds [e.g. 2,2'-azobis(isobutyronitrile)], azoamide compounds and azoamidine compounds. One of these thermal polymerization initiators may be used alone, or two or more of these thermal polymerization initiators may be mixed and used as necessary.

Examples of the photopolymerization initiator include benzoins (e.g. benzoin, and benzoin alkyl ethers such as benzoin methyl ether, benzoin ethyl ether and benzoin isopropyl ether); acetophenones (e.g. acetophenone, 1-hydroxy-cyclohexyl phenyl ketone and 2-hydroxy-2-methyl-1-phenylpropan-1-one); aminoacetophenones {e.g. 2-methyl-1-[4-(methylthio)phenyl]-2-morpholinoaminopropane-1-one}; anthraquinones (e.g. anthraquinone and 2-methylanthraquinone); thioxanthones (e.g. 2,4-dimethylthioxanthone, 2,4-diethylthioxanthone and 2-chlorothioxanthone); ketals (e.g. acetophenone dimethyl ketal and benzyl dimethyl ketal); benzophenones (e.g. benzophenone); and xanthones. One of these photopolymerization initiators may be used alone, or two or more of these photopolymerization initiators may be mixed and used as necessary.

The photopolymerization initiator may be used in combination with a photosensitizer. Examples of the photosensitizer that can be used in combination include tertiary amines {e.g. trialkylamines, trialkanolamines (e.g. triethanolamine), dialkylaminobenzoic acid alkyl esters such as ethyl N,N-dimethylaminobenzoate [e.g. ethyl p-(dimethylamino) benzoate] and amyl N,N-dimethylaminobenzoate [e.g. amyl p-(dimethylamino)benzoate], bis(dialkylamino) benzophenones such as 4,4-bis(diethylamino)benzophenone (Michler's ketone), and dialkylaminobenzophenones such as 4-(dimethylamino)benzophenone, etc.}. One of these photosensitizers may be used alone, or two or more of these photosensitizers may be mixed and used as necessary.

The use amount of the polymerization initiator is normally 0.1 to 30 parts by weight, preferably 1 to 20 parts by weight, more preferably 1.5 to 10 parts by weight based on 100 parts by weight of a (meth)acrylate compound represented by the general formula (3) (based on 100 parts by weight of the total of a (meth)acrylate compound represented by the general formula (3) and other polyfunctional (meth)acrylates when other polyfunctional (meth)acrylates are used in combination). When a photosensitizer is used in combination with the polymerization initiator (photopolymerization initiator), the use amount of the photosensitizer is 5 to 200 parts by weight, preferably 10 to 150 parts by weight, more preferably 20 to 100 parts by weight based on 100 parts by weight of the polymerization initiator (photopolymerization initiator).

Examples of the diluent that may be contained in the curable composition of the present invention include reactive diluents and/or nonreactive diluents (solvents). Specific examples of the reactive diluent include (meth)acryl-based monomers such as polymerizable monomer alkyl (meth) acrylates [e.g. $C_{1-20}$ alkyl (meth)acrylates, preferably $C_{1-10}$ alkyl (meth)acrylates, such as methyl (meth)acrylate, ethyl (meth)acrylate and butyl (meth)acrylate]; cycloalkyl (meth)acrylates [e.g. $C_{5-8}$ cycloalkyl (meth)acrylates such as cyclohexyl (meth)acrylate]; aryl (meth)acrylates [e.g. phenyl (meth)acrylate]; hydroxyalkyl (meth)acrylates [e.g. hydroxyl $C_{2-10}$ alkyl (meth)acrylates such as 2-hydroxyethyl (meth)acrylate, 2-hydroxypropyl (meth)acrylate and 2-hydroxybutyl (meth)acrylate]; (poly)oxyalkylene glycol mono (meth)acrylates ((poly)oxy$C_{2-6}$ alkylene glycol mono(meth) acrylates such as diethylene glycol mono(meth)acrylate, methoxy tetraethylene glycol mono(meth)acrylate and polyethylene glycol mono (meth) acrylate); alkoxyalkyl (meth) acrylates [e.g. $C_{1-4}$ alkoxyalkyl (meth)acrylates such as 2-methoxyethyl (meth)acrylate and 3-methoxybutyl (meth) acrylate]; N-substituted (meth)acrylamides (e.g. N,N-di-$C_{1-4}$ alkyl (meth)acrylamides such as N,N-dimethyl(meth) acrylamide and N-hydroxy-$C_{1-4}$ alkyl (meth)acrylamides such as N-methylol (meth)acrylamide); aminoalkyl (meth) acrylates (e.g. N,N-dimethylaminoethyl acrylate); glycidyl (meth)acrylate; and tetrahydrofurfuryl (meth)acrylate, and non-(meth)acryl-based monomers (e.g. aromatic vinyl-based monomers (e.g. styrene). One of these reactive diluents may be used alone, or two or more of these reactive diluents may be mixed and used as necessary.

When a reactive diluent is used, the use amount thereof is normally 1 to 1000 parts by weight, preferably 5 to 500 parts by weight, more preferably 10 to 200 parts by weight based on 100 parts by weight of a (meth)acrylate compound represented by the general formula (3) (based on 100 parts by weight of the total of a (meth)acrylate compound represented by the general formula (3) and other polyfunctional (meth)acrylates when other polyfunctional (meth)acrylates are used in combination).

Examples of the nonreactive diluent include aliphatic hydrocarbons, ketones, aromatic hydrocarbons, glycol ethers, esters and petroleum-based solvents. Examples of the nonreactive diluent include hexane, heptane and octane as aliphatic hydrocarbons; ethyl methyl ketone and cyclohexanone as ketones; toluene and xylene as aromatic hydrocarbons; ethylcellosolve, methylcellosolve, carbitol, methyl carbitol and propylene glycol monomethyl ether as glycol ethers; methyl acetate, ethyl acetate, butyl acetate, cellosolve acetate, butylcellosolve acetate, carbitol acetate, butyl carbitol acetate, propylene glycol monomethyl ether acetate and propylene carbonate as esters; and petroleum ether, petroleum naphtha and solvent naphtha as petroleum-based solvents. One of these nonreactive diluents may be used alone, or two or more of these nonreactive diluents may be mixed and used as necessary.

When a nonreactive diluent is used, the use amount thereof is normally 1 to 500 parts by weight, preferably 20 to 300 parts by weight, more preferably 30 to 200 parts by weight based on 100 parts by weight of a (meth)acrylate compound represented by the general formula (3) (based on 100 parts by weight of the total of a (meth)acrylate compound represented by the general formula (3) and other polyfunctional (meth)acrylates when other polyfunctional (meth)acrylates are used in combination).

The curable composition of the present invention may contain common additives, e.g. colorants, stabilizers (heat stabilizer, antioxidant, ultraviolet absorber and the like), fillers, antistatic agents, flame retardants, a flame-retardant aids, leveling agents, silane coupling agents and polymerization inhibitors (or thermal polymerization inhibitor) in addition to the above-described other polyfunctional (meth) acrylates, polymerization initiator and diluent. One of these additives may be used alone, or two or more of these additives may be mixed and used as necessary.

<Cured Product Obtained by Curing Curable Composition>

The cured product obtained by curing a curable composition containing a (meth)acrylate compound represented by the general formula (3) according to the present invention is produced by curing the above-mentioned curable composition of the present invention. For example, a film-shaped cured product can be produced in the following manner: a curable composition containing a (meth)acrylate compound represented by the general formula (3) is applied to a substrate to form a coating film (or thin film), and a curing treatment is then performed. The thickness of the film-shaped coating film (or thin film) can be selected according to the intended use, and is, for example, 0.1 to 1000 μm, preferably 1 to 500 μm, more preferably 5 to 300 μm. In addition, a cured product having a three-dimensional shape (e.g. prism shape or lens shape) can be produced by using cast molding, a 3D printer, or the like. Prior to the curing treatment, the viscosity of the curable composition containing a (meth)acrylate compound represented by the general formula (3) may be reduced by heating as necessary.

Examples of the curing treatment include a heating treatment and a photoirradiation treatment. In addition, the heating treatment and the photoirradiation treatment may be combined. The heating temperature at which the heating treatment is performed is 50 to 250° C., preferably 60 to 200° C., more preferably 70 to 150° C. In addition, in the photoirradiation treatment (exposure treatment), the amount of photoirradiation energy varies depending on the intended use, the thickness of a coating film and the like, but is normally 0.1 to 10000 mJ/cm$^2$, preferably 1 to 8000 mJ/cm$^2$, more preferably 10 to 5000 mJ/cm$^2$.

The (meth)acrylate compound represented by the general formula (3) according to the present invention is excellent in compatibility or solubility with a diluent such as an organic solvent or a monofunctional (meth)acrylate, so that a cured product can be easily produced without necessity to perform dilution with a large amount of a diluent or heating at a high temperature for reduction of the viscosity. Thus, a cured product can be more easily produced as compared to a case where a difunctional (meth)acrylate compound derived from a previously known bisphenol compound having a fluorene skeleton or a binaphthyl skeleton is used, and a cured product capable of sufficiently exhibiting properties (high refractive index, high heat resistance and the like) of a (meth)acrylate compound represented by the general formula (3) can be obtained.

<Epoxy Resin>

An epoxy resin of the present invention is an epoxy resin including in the main chain a constituent unit derived from a bisphenol represented by the general formula (1) (hereinafter, sometimes referred to as an epoxy resin of the present invention). The content ratio of the constituent unit derived from a bisphenol represented by the general formula (1) is 10 to 100 mol %, preferably 20 to 100 mol %, especially preferably 30 to 100 mol % in terms of a molar ratio based on the total of constituent units in the epoxy resin.

Examples of the epoxy resin of the present invention include epoxy resins which are obtained by reacting epihalohydrin with a bisphenol represented by the general formula (1) and which are represented by the general formula (4); and epoxy resins obtained by reacting a bisphenol represented by the general formula (1) with an epoxy compound having other structure.

Examples of the alkyl group in the substituents ($R_1$ to $R_4$) in the general formula (4) include optionally branched alkyl groups such as a methyl group, an ethyl group, a propyl group and an isopropyl group, and cyclic alkyl groups such as a cyclopentyl group and a cyclohexyl group. Examples of the aryl group include aromatic groups optionally having a substituent, such as a phenyl group and a tolyl group. Examples of the halogen atom include a fluorine atom, a chlorine atom, a bromine atom and an iodine atom. Among these substituents shown as examples, optionally branched alkyl groups having 1 to 4 carbon atoms are preferable for the same reason as described above for the preferred aspect of a bisphenol represented by the general formula (1).

$k_1$ to $k_4$ representing the number of substituents ($R_1$ to $R_4$) are the same or different, and each represent 0 or an integer of 1 to 4, preferably 0 or an integer of 1 to 2, more preferably 0 or 1 for the same reason as described above for the preferred aspect of a bisphenol represented by the general formula (1). When at least one of $k_1$ to $k_4$ is 2 or more, the corresponding substituents may be the same or different.

$n_1$ and $n_2$ representing the number of methylene groups connecting a phenyl group having a hydroxyl group and the other phenyl group are the same or different, and each represent an integer of 1 to 4, preferably 1 or 2, more preferably 1 for the same reason as described above for the preferred aspect of a bisphenol represented by the general formula (1).

p representing the polymerization number of the epoxy resin represented by the general formula (4) is 0 or an integer of 1 or more, preferably 0 or an integer of 1 to 10, more preferably 0 or an integer of 1 or 2, most preferably 0 or 1. It is possible to obtain an epoxy resin having a single polymerization number p by purification, but a mixture of epoxy resins having a plurality of polymerization numbers p is normally used as an epoxy resin.

When in the mixture of epoxy resins having a plurality of polymerization numbers p, the ratio of epoxy resins having a polymerization number p of more than 3 increases, the softening point may be excessively high, leading to deterioration of handling property during production and formation of an epoxy resin composition, and compatibility may be deteriorated, resulting in occurrence of the problem that the addition amount is restricted in formation of an epoxy resin composition. Thus, in the case of a mixture of epoxy resins having a plurality of polymerization numbers p, the average polymerization number (average value of p) of the epoxy resins is preferably less than or equal to 2, more preferably less than or equal to 1.

The epoxy resin of the present invention may contain as impurities a monoglycidyl compound as an intermediate, a small amount of hydrolyzable chlorine, α-glycol and the like, but as long as properties as an epoxy resin are not impaired, the epoxy resin is not required to be specially purified, and may be a mixture with impurities.

The epoxy resin of the present invention has a 5% weight loss temperature of normally 300° C. or higher, particularly 320° C. or higher as measured under conditions as described later, and are therefore suitably used for power devices and semiconductor sealing materials which require thermal tolerance. In addition, the epoxy resin has a high refractive index of normally 1.60 or more, particularly 1.61 or more, more particularly 1.62 or more as measured under conditions as described later, therefore can be suitably used for optical members. Further, since the epoxy resin of the present invention has high solvent solubility and a low viscosity, not only the epoxy resin can be used in various applications such as adhesives, coatings and civil engineering materials, but also the epoxy resin can be reacted with another compound such as acrylic acid to form a raw material of a resin having a new structure.

<Method for Producing Epoxy Resin>

The epoxy resin of the present invention can be produced by, for example, a method in which a bisphenol represented by the general formula (1) is reacted with epihalohydrin, or a method in which a bisphenol represented by the general formula (1) is reacted with an epoxy compound having another structure. When a bisphenol represented by the general formula (1) is reacted with epihalohydrin, it is possible to produce an epoxy resin represented by the general formula (4), among fluorene-based epoxy resins including in the main chain a constituent unit derived from a bisphenol represented by the general formula (1). Hereinafter, the method for producing an epoxy resin represented by the general formula (4) will be described in detail.

Examples of the method for reacting a bisphenol represented by the general formula (1) with epihalohydrin include a method in which a bisphenol represented by the general formula (1) is mixed with epihalohydrin, an alkali metal hydroxide is then added to the mixture at 20 to 120° C., preferably 40 to 80° C., and the mixture is then reacted at 20 to 120° C., preferably 40 to 100° C. (hereinafter, the reaction is sometimes referred to as an epoxidation reaction). The alkali metal hydroxide may be added at a time, but it is preferable that for maintaining the above-mentioned temperature, the alkali metal hydroxide be added continuously over a certain period of time, or added in portions in a necessary amount.

Examples of the alkali metal hydroxide to be used in the epoxidation reaction include sodium hydroxide, potassium hydroxide and the like, and the use amount thereof is normally 0.8 to 10.0 mol, preferably 2.0 to 5.0 mol based on 1 mole of the bisphenol represented by the general formula (1). An aqueous solution of the alkali metal hydroxide may be used. When an aqueous solution of the alkali metal hydroxide is used, a method may be employed in which the aqueous solution is continuously added into the reaction system, water and epihalohydrin are continuously distilled off under reduced pressure or normal pressure, and then the distillate is separated, so that water is removed while epihalohydrin is continuously fed back into the reaction system.

Specific examples of the epihalohydrin to be used in the epoxidation reaction include epichlorohydrin and epibromohydrin, and the use amount thereof is normally 2 to 40 mol, preferably 4 to 30 mol based on 1 mole of a bisphenol represented by the general formula (1). p representing the polymerization number of an epoxy resin represented by the general formula (4) can be adjusted by the molar ratio of the bisphenols represented by the general formula (1) and epihalohydrin. Specifically, when epihalohydrin is used in an excessively large amount with respect to a bisphenol represented by the general formula (1), a compound having a polymerization number p of 0 is obtained as a main component, and by reducing the use amount of epihalohydrin, the ratio of a compound having a polymerization number p of more than 0 can be increased.

At the time of carrying out the epoxidation reaction, the reaction rate can be improved by further adding a quaternary ammonium salt or quaternary phosphonium salt such as tetramethylammonium chloride, tetramethylammonium bromide, tetrabutylammonium bromide, benzyltrimethylammonium chloride, benzyltriethylammonium chloride, amyltriphenylphosphonium bromide, benzyltriphenylphosphonium bromide, benzyltriphenylphosphonium chloride or allyltriphenylphosphonium chloride. The addition amount of the salt is normally 0.01 to 0.50 mol, preferably 0.02 to 0.20 mol based on 1 mole of a bisphenol represented by the general formula (1). When the salt is used, normally the salt is added before the alkali metal hydroxide is added to the mixture of a bisphenols represented by the general formula (1) and epihalohydrin.

After the epoxidation reaction, the reaction liquid containing the epoxy resin represented by the general formula (4) may be directly formed into an epoxy resin composition by adding a curing agent, a reaction diluent as necessary, a curing accelerator, a solvent, and additives as necessary, or may be reacted with acrylic acid to form an epoxy acrylate resin.

In addition, the purity of the epoxy resin represented by the general formula (4) can be improved by subjecting the resulting reaction liquid to filtration or washing with water as necessary to remove undissolved components, inorganic salts and alkali metal hydroxides, or removing epihalohydrin at 100 to 180° C. and an internal pressure of 30 mmHg or less, preferably an internal pressure of 10 mmHg or less, under heating and reduced pressure when epihalohydrin is used in an excessive amount.

Further, for obtaining an epoxy resin with a reduced amount of a hydrolyzable halogen, the reaction liquid containing an epoxy resin represented by the general formula (4) or the epoxy resin represented by the general formula (4) is dissolved in an aromatic hydrocarbon such as benzene, toluene or xylene, and an aqueous solution of an alkali metal hydroxide such as sodium hydroxide or potassium hydroxide is added to carry out a ring closure reaction, so that the ring can be reliably closed. Here, the use amount of the alkali metal hydroxide is normally 0.01 to 15.0 mol, preferably 0.20 to 7.5 mol based on 1 molar equivalent of hydroxyl groups of a bisphenol used in epoxidation and represented by the general formula (1), and the reaction temperature is normally 20 to 120° C.

After completion of the ring closure reaction, tar component and salts which are by-products, are removed by filtration or removed by washing with water, the solution containing an epoxy resin represented by the general formula (4) is then neutralized by adding phosphoric acid, sodium phosphate, oxalic acid, acetic acid, carbonic acid or the like so that the solution has a pH of 4.0 to 8.0, washing with water is repeated, and filtration is then performed, and further, the solvent used in the above-mentioned reaction, extraction and the like is distilled off to obtain an epoxy resin represented by the general formula (4) and having a reduced amount of a hydrolyzable halogen.

<Epoxy Resin Composition Containing Epoxy Resin>

Hereinafter, an epoxy resin composition containing the above-described epoxy resin including in the main chain a constituent unit derived from a bisphenol represented by the general formula (1) (hereinafter, sometimes referred to as an epoxy resin composition of the present invention) will be described in detail. The epoxy resin composition of the present invention may contain a curing agent, a reaction diluent, a curing accelerator, a solvent, a common additive (e.g. glass fiber or inorganic filler, flame retardant, sizing agent, coupling agent, coloring material, stabilizer, antistatic agent and the like), and so on. In addition, the epoxy resin composition may contain other epoxy resins.

As the curing agent which may be contained in the epoxy resin composition of the present invention, curing agents for epoxy resin which are commonly used, such as various phenolic resins and acid anhydrides, amines, amides, imidazoles, heat/photo-cationic polymerization initiators, organic phosphorus compounds, guanidine derivatives, organic acid dihydrazides, halogenated boron amine complexes, polymercaptan-based curing agents, isocyanate-based curing agents and block isocyanate-based curing agents can be used. Specific examples of the curing agent include bisphenol A, bisphenol F, 4,4'-dihydroxydiphenylmethane, 4,4'-dihydroxydiphenyl ether, 1,4-bis (4-hydroxyphenoxy)benzene, 1,3-bis(4-hydroxyphenoxy)benzene, 4,4'-dihydroxydiphenyl sulfide, 4,4'-dihydroxydiphenyl ketone, 4,4'-dihydroxydiphenyl sulfone, 4,4'-dihydroxybiphenyl, 2,2'-dihydroxybiphenyl, phenol novolac, modified products thereof, 1,12-diaminododecane, diaminodiphenylmethane, diethylenetriamine, triethylenetetramine, diaminodiphenylsulfone, isophoronediamine, dicyandiamide, 4-methylcyclohexane-1,2-dicarboxylic anhydride, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, 2-phenylimidazole, 2-ethyl-4-methylimidazole, 2-phenyl-4-methylimidazole, 1-benzyl-2-methylimidazole, 1-benzyl-2-phenylimidazole, 1-cyanoethyl-2-undecylimidazole, 1-cyano-2-phenylimidazole, 1-cyanoethyl-2-undecylimidazole trimellitate, 1-cyanoethyl-2-phenylimidazolium trimellitate, 2,4-diamino-6-[2-(2-methyl-1-imidazolyl)ethyl]-1,3,5-triazine, 2-phenylimidazoleisocyanuric acid adducts, 2-phenyl-4,5-dihydroxymethylimidazole, 2-phenyl-4-methyl-5-hydroxymethylimidazole and $BF_3$-amine complexes. One of these curing agents may be used alone, or two or more of these curing agents may be used in combination.

The use amount of the curing agent is preferably 0.5 to 1.5 equivalents, more preferably 0.7 to 1.2 equivalents based on 1 equivalent of all epoxy groups in the epoxy resin composition of the present invention. When the curing agent is used in an amount of 0.5 equivalents or more and 1.5 equivalents or less, the epoxy resin composition can be perfectly cured, and as a result, a cured product having favorable curing physical properties can be obtained.

Examples of other epoxy resins that may be contained in the epoxy resin composition of the present invention include bisphenol-based epoxy resins such as bisphenol A-type epoxy resins and bisphenol F-type epoxy resins; polyfunctional phenol-based epoxy resins such as biphenyl-type epoxy resins and novolac-type epoxy resins; naphthol-based epoxy resins; and epoxy resins having a fluorene skeleton other than the epoxy resin of the present invention. One of these epoxy resins may be used alone, or two or more of these epoxy resins may be combined.

Specific examples of the curing accelerator that may be contained in the epoxy resin composition of the present invention include imidazoles such as 2-methylimidazole, 2-ethylimidazole and 2-ethyl-4-methylimidazole; tertiary amines such as 2-(dimethylaminomethyl)phenol and 1,8-diaza-bicyclo(5,4,0)undecene-7; and phosphines such as triphenylphosphine. When the curing accelerator is used, the use amount thereof is normally 0.2 to 5.0 parts by weight based on 100 parts by weight of all epoxy resins in the epoxy resin composition of the present invention.

The reactive diluent which may be contained in the epoxy resin composition of the present invention is a low-viscosity epoxy compound to be added for adjusting the viscosity, and particularly preferably a di-or-more-functional low-viscosity epoxy compound. Examples of the reactive diluent include diglycidyl ether, butanediol diglycidyl ether, diglycidyl aniline, neopentyl glycol diglycidyl ether, cyclohexane dimethanol diglycidyl ether, alkylene diglycidyl ethers, polyglycol diglycidyl ether, polypropylene glycol diglycidyl ether, trimethylolpropane triglycidyl ether, glycerol triglycidyl ether, 4-vinylcyclohexene monoxide, vinylcyclohexene dioxide, methylated vinylcyclohexene dioxide, phenyl glycidyl ether, 4-tert-butylphenyl glycidyl ether and o-phenylphenyl glycidyl ether. One of these reactive diluents may be used alone, or two or more of these reactive diluents may be mixed and used as necessary. The reactive diluent can be used within the bounds of not hindering the object of the present invention, and can be used with the epoxy resin composition containing the reactive diluent in an amount of, for example, 0 to 50% by weight.

Examples of the solvent which may be contained in the epoxy resin composition of the present invention include alcohols such as methanol and ethanol; ethers such as tetrahydrofuran; glycol ethers such as ethylene glycol monomethyl ether, ethylene glycol monoethyl ether, ethylene glycol monobutyl ether, ethylene glycol dimethyl ether, diethylene glycol monomethyl ether, diethylene glycol monoethyl ether, diethylene glycol dimethyl ether, diethylene glycol diethyl ether and diethylene glycol monobutyl ether; alkylene glycol monoalkyl ether acetates such as methylcellosolve acetate, ethylcellosolve acetate, butylcellosolve acetate, propylene glycol methyl ether acetate and 3-methoxybutyl-1-acetate; aromatic hydrocarbons such as toluene and xylene; ketones such as methyl ethyl ketone, methyl isobutyl ketone, methyl amyl ketone, cyclohexanone and 4-hydroxy-4-methyl-2-pentanone; and esters such as ethyl 2-hydroxypropionate, methyl 2-hydroxy-2-methylpropionate, ethyl 2-hydroxy-2-methylpropionate, ethyl ethoxyacetate, ethyl hydroxyacetate, methyl 2-hydroxy-2-methylbutanoate, methyl 3-methoxypropionate, ethyl 3-methoxypropionate, methyl 3-ethoxypropionate, ethyl 3-ethoxypropionate, ethyl acetate, butyl acetate, methyl lactate and ethyl lactate. One of these solvents may be used alone, or two or more of these solvents may be mixed and used as necessary.

<Cured Product Obtained by Curing Epoxy Resin Composition>

Subsequently, a method for producing a cured product obtained by curing the above-described epoxy resin composition of the present invention, and the cured product will be described in detail.

The cured product of the epoxy resin composition of the present invention can be obtained by, for example, sufficiently mixing the epoxy resin of the present invention, a curing agent, other epoxy resins, and additives to be added as necessary, such as a reaction diluent, a curing accelerator, a solvent, an inorganic filler and a flame retardant until the mixture is homogeneous, thus obtaining an epoxy resin composition, and pouring the obtained epoxy resin composition into a mold, casting the epoxy resin composition, and then curing the epoxy resin composition by light and/or heat. For example, when the epoxy resin composition is cured by heat, the curing temperature varies depending on the curing agent to be used and other epoxy resins to be used in combination, but the curing temperature is normally in a range of 25 to 250° C., preferably in a range of 80 to 240° C., more preferably in a range of 100 to 230° C. As a curing method, the epoxy resin composition can be cured at a time at a high temperature, but it is preferable to elevate the temperature stepwise, so that a curing reaction proceeds. Specifically, initial curing is performed at a temperature between 80° C. and 150° C., and post-curing is then performed at a temperature between 100° C. to 230° C.

The "curing" mentioned in the present invention normally means that an epoxy resin, a curing agent, and other components to be blended as necessary are mixed, and the epoxy resin composition is then intentionally cured by heat and/or light. The degree of the curing may be controlled according to desired physical properties and an intended use. As a degree to which curing proceeds, the epoxy resin composition may be fully cured, or semi-cured. The rate at which the epoxy group and the curing agent react is normally 5 to 95%.

<Molded Product of Invention>

A molded product of the present invention includes at least one cured product or resin selected from the group consisting of the polyarylate resin, a cured product obtained by curing the curable composition containing a (meth) acrylate compound, and a cured product obtained by curing the epoxy resin composition (hereinafter, sometimes referred to as a cured product etc. of the present invention). For obtaining the molded product of the present invention, a method such as a casting method, injection molding method, an injection compression molding method, an extrusion molding method, a transfer molding method, a blow molding method or a pressure molding method can be used, but the method is not particularly limited, and may be appropriately selected according to an intended use. An example of the method will be described below.

The casting method is a so-called solution casting method, where the cured product etc. of the present invention is dissolved in an organic solvent, the solution is applied to a metallic drum or belt, or a film substrate composed of a resin different from that of the cured product etc. of the present invention, the organic solvent is then distilled off, and the coating film is peeled off from the substrate or the like to obtain a film containing the cured product etc. of the present invention.

The organic solvent to be used in the solution casting method is not particularly limited, and examples thereof include N-methylpyrrolidone (NMP), N,N-dimethylformamide, methylene chloride, 1,2-dichloroethane, chloroform, carbon tetrachloride, chlorobenzene, 1,1,2,2-tetrachloroethane, 1,1,1-trichloroethane, o-dichlorobenzene, m-dichlorobenzene, toluene, benzene, xylene, THF, 1,4-dioxane and 1,3-dioxolane. In particular, from the viewpoint of being free from a halogen, NMP, toluene, benzene, xylene, THF, 1,4-dioxane and 1,3-dioxolane are preferable, and toluene or tetrahydrofuran is more preferable.

The thickness of such a film can be selected from a range of about 1 to 1000 μm according to an intended use, and may be, for example, 1 to 200 μm, preferably 5 to 150 μm, more preferably about 10 to 120 μm.

Alternatively, the molded product can be produced by deposition (or molding) using an extrusion molding method, a calendar molding method or the like. In addition, when an injection molding method or the like is applied, it is possible to produce molded products having various shapes.

Examples of the shape of the molded product include two-dimensional structures (film shape, sheet shape, plate shape and the like), three dimensional structures (pipe shape, rod shape, tubular shape, hollow shape and the like). Molded products including the cured product etc. of the present invention have excellent optical properties such as transparency and a high refractive index, and are therefore suitably used as optical members.

EXAMPLES

Hereinafter, the present invention will be described more in detail by way of examples etc., but the present invention is not limited to the examples. In the following examples, etc., measurement values were obtained in accordance with the following methods and measurement conditions. In addition, the production ratio (residual ratio) and purity (HPLC purity) of each component described in examples etc. each correspond to area percentages in HPLC measured under the following conditions.

[1] HPLC Analysis (1-1) Conditions for HPLC Analysis of Bisphenol

Apparatus: LC-20A manufactured by Shimadzu Corporation

Column: XBridge Shield RP 18 (3.5 μm, 4.6 mm φ×250 mm) manufactured by Waters Corporation Mobile phase: liquid A: pure water, liquid B: acetonitrile. Analysis was performed while the concentration of liquid B was changed as described below.

Concentration of liquid B: 70% (0 min)→70% (10 min)→100% (20 min)→100% (30 min)

Flow rate: 1.0 ml/min

Column temperature: 40° C.

Detection wavelength: 254 nm (1-2) Conditions for HPLC Analysis of (Meth)Acrylate Compound Apparatus: LC-20A manufactured by Shimadzu Corporation Column: L-Column ODS (5 μm, 4.6 mm φ×250 mm) manufactured by Chemicals Evaluation and Research Institute, Japan Mobile phase: liquid A: 30% methanol water, liquid B: methanol. Analysis was performed while the concentration of liquid B was changed as described below.

Concentration of liquid B: 30% (0 min)→100% (10 min)→100% (35 min)

Flow rate: 1.0 ml/min

Column temperature: 40° C.

Detection wavelength: 254 nm (1-3) Conditions for HPLC Analysis of Epoxy Resin

Apparatus: LC-2010AHT manufactured by Shimadzu Corporation

Column: SUMIPAX ODS A-212 (5 μm, 6.0 mm φ×150 mm) manufactured by Sumika Chemical Analysis Service, Ltd.

Mobile phase: liquid A: water, liquid B: acetonitrile. Analysis was performed while the concentration of liquid B was changed as described below.

Concentration of liquid B: 50% (0 min)→100% (40 min)→50% (60 min)

Mobile phase flow rate: 1.0 ml/min

Column temperature: 40° C.

Detection wavelength: 254 nm

[2] NMR Measurement $^1$H-NMR and $^{13}$C-NMR were recorded by JEOL-ESC 400 spectrometer with tetramethylsilane used as an internal standard and chloroform-d1 ($CDCl_3$) or acetone-d6 ($CD_3COCD_3$) as a solvent.

[3] LC-MS measurement (3-1) Conditions for LC-MS Measurement of (Meth) Acrylate Compound Apparatus: Xevo G 2 Q-Tof manufactured by Waters Corporation Column: L-Column 2 ODS (2 m, 2.1 mm φ×100 mm) manufactured by Chemicals Evaluation and Research Institute, Japan Column temperature: 40° C.

Detection wavelength: UV 210-500 nm

Mobile phase: liquid A=pure water, liquid B=acetonitrile. Analysis was performed while the concentration of liquid B was changed as described below.

Concentration of liquid B: 80% (0 min)→100% (15 min)→100% (25 min)

Mobile phase flow rate: 0.3 ml/min

Detection method: Q-Tof

Ionization method: APCI (+) method

Ion Source: voltage (+): 2.0 kV, temperature: 120° C.

Sampling Cone: voltage: 30 V, gas flow: 50 L/h

Desolvation Gas: temperature: 500° C., gas flow 1000 L/h (3-2) Conditions for LC-MS Measurement of Epoxy Resin Apparatus: Xevo G 2 Q-Tof manufactured by Waters Corporation Column: ACQUITY UPLC BEH C 18 (1.7 μm, 2.1 mm φ×100 mm) manufactured by Waters Corporation Column temperature: 40° C.

Detection wavelength: UV 210-500 nm

Mobile phase: Solution A=10 mM ammonium acetate water, solution B=acetonitrile. Analysis was performed while the concentration of liquid B was changed as described below.

Concentration of liquid B: 80% (0 min)→100% (10 min)→100% (15 min)

Mobile phase flow rate: 0.3 ml/min

Detection method: Q-Tof

Ionization method: APCI (+) method

Ion Source: voltage (+): 2.0 kV, temperature: 120° C.

Sampling Cone: voltage: 30 V, gas flow: 50 L/h

Desolvation Gas: temperature: 500° C., gas flow 1000 L/h

[4] Melting Point (Melt Endothermic Maximum Temperature in Differential Scanning Calorimetry (DSC)) and Glass Transition Temperature 5 mg of a sample was precisely weighed, and taken in an aluminum pan, measurement was performed under the following operation conditions with aluminum oxide as a control using a differential scanning calorimeter (DSC 7020 manufactured by SII NanoTechnology Inc.), and the detected melt endothermic maximum temperature was defined as a melting point. For a sample (amorphous material, resin or the like) in which a melt endothermic peak was not detected, the intersection of tangent lines at an inflection point was defined as a glass transition temperature (Tg).

(Operating Conditions)

Temperature elevation rate: 10° C./min (for bisphenol and (meth)acrylate compound) and 20° C./min (for polyarylate resin)

Measurement range: 30 to 250° C. (for bisphenol), 150 to 250° C. (for polyarylate resin) and −30 to 350° C. (for (meth)acrylate compound)

atmosphere: Open, nitrogen: 40 ml/min

[5] Refractive Index and Abbe Number

The refractive index of each of the bisphenol, the polyarylate resin, the (meth)acrylate compound and the epoxy resin is a value determined using the following method and conditions. In addition, the Abbe number of each of the (meth)acrylate compound and the epoxy resin was calculated on the basis of the refractive index measured using the following method and conditions.

Apparatus: Abbe refractometer ("multiwavelength Abbe refractometer DR-2M" manufactured by ATAGO CO., LTD.)

Measurement wavelength: 589 nm (refractive index), 486, 589, 656 nm (Abbe number)

Measurement temperature: 20° C.

Refractive index of bisphenol: The bisphenol was dissolved in N-methyl-2-pyrrolidone (hereinafter, sometimes referred to as NMP) to prepare 5 wt %, 10 wt % and 15 wt % solutions, and the refractive index was measured for each of the solutions using the above-mentioned apparatus and conditions. Next, an approximate curve was derived from the obtained three measured values, and a value obtained by extrapolating the curve at 100% by weight was defined as a refractive index of each bisphenol.

Refractive index of polyarylate resin: A polyarylate resin powder was dissolved in NMP to prepare 1 wt %, 3 wt % and 5 wt % solutions, and the refractive index was measured for each of the solutions using the above-mentioned apparatus and conditions. Next, an approximate curve was derived from the obtained three measured values, and a value obtained by extrapolating the curve at 100% by weight was defined as a refractive index of each polyarylate resin.

Refractive index and Abbe number of (meth)acrylate compound: Each (meth)acrylate compound was dissolved in NMP to prepare a 5 wt %, 10 wt % and 15 wt % solutions (for Comparative Examples 4 and 5, 1 wt %, 3 wt % and 5 wt % solutions were prepared because the (meth)acrylate compound was hardly soluble in an organic solvent), and the refractive index at each wavelength was measured for each of the solutions using the above-mentioned apparatus and conditions. Next, an approximate curve was derived from the obtained three measured values, a value obtained by extrapolating the curve at 100% by weight was defined as a refractive index of each (meth)acrylate compound at each wavelength, and the Abbe number was calculated on the basis of the refractive index at each wavelength, which was determined as described above.

Refractive index and Abbe number of epoxy resin: Each epoxy resin was dissolved in NMP to prepare 5 wt %, 10 wt % and 15 wt % solutions, and the refractive index at each wavelength was measured for each of the solutions using the above-mentioned apparatus and conditions. Next, an approximate curve was derived from the obtained three measured values, a value obtained by extrapolating the curve at 100% by weight was defined as a refractive index of each epoxy resin at each wavelength, and the Abbe number was calculated on the basis of the refractive index at each wavelength, which was determined as described above.

[6] 5% Weight Loss Temperature

Using a thermogravimetric instrument (TGA-50 from Shimadzu Corporation), measurement was performed with the temperature elevated at a rate of 10° C./min from room temperature to 500° C. under a nitrogen gas stream.

[7] Weight Average Molecular Weight (Mw)

By gel permeation chromatography (GPC), analysis was performed under the following conditions to determine the weight average molecular weight (Mw) in terms of polystyrene.

Apparatus: EcoSEC HLC-8320 GPC manufactured by TOSOH CORPORATION
Column: four columns of TSKguardcolumn SuperHZ-L, TSKgel SuperHZ 4000, TSKgel SuperHZ 2500 and TSKgel SuperHZ 1000
Flow rate: 0.35 mL/min
Mobile phase: THF
Column temperature: 40° C.
Detector: RI

[8] Fluidity Test (Melt Flow Rate (MFR))

The discharge amount of the polyarylate resin extruded from an orifice by applying a load of 2.160 kg to the polyarylate resin melted in a cylinder (heating cylinder) was converted to a weight per 10 minutes (unit: g/10 min).

<Test Conditions>
Apparatus: Melt Indexer Model I (manufactured by TESTER SANGYO CO., LTD.)
Load: 2.160 kg
Test temperature: 285° C. and 360° C.

[9] Solubility Test (9-1) Solubility Test of Polyarylate Resin

The polyarylate resin was mixed with each of the solvents shown in Table 2 at each of the following concentration, the mixture was stirred for 1 hour, and then solubility was evaluated on the basis of the following evaluation criteria.

<Evaluation Criteria>
○: The sample is dissolved at room temperature at a concentration of 20% by weight.
Δ: The sample is dissolved at a concentration of 10% by weight at room temperature.
x: The sample is not dissolved at room temperature.

(9-2) Solubility Test of (Meth)Acrylate Compound 30 parts by weight of the (meth)acrylate compound and 70 parts by weight of each of the diluents (solvent or monofunctional acrylate) shown in Table 3 were mixed, and solubility was evaluated on the basis of the following evaluation criteria.

<Evaluation Criteria>
○: The sample is dissolved at room temperature.
Δ: The sample is dissolved when heated, and crystals are not precipitated even when the sample is cooled.
x: The sample is dissolved when heated, but crystals are precipitated when the sample is cooled, or the sample is not dissolved even when heated.

(9-3) Solubility Test of Epoxy Resin 30 parts by weight of each epoxy resin is mixed with 70 parts by weight of each of the solvents shown in Table 4, and solubility was evaluated on the basis of the following evaluation criteria.

<Evaluation Criteria>
○: The sample is dissolved at room temperature.
Δ: The sample is dissolved when heated, and crystals are not precipitated even when the sample is cooled.
x: The sample is dissolved when heated, but crystals are precipitated when the sample is cooled, or the sample is not dissolved even when heated.

[10] Fourier transform infrared spectrophotometry (FT-IR) measurement

FT-IR measurement was performed under the following conditions.

Apparatus: FT-IR spectrophotometer (IRTracer-100 manufactured by Shimadzu Corporation)
Measurement method: KBr tablet method
Measurement conditions: resolution: 2 $cm^{-1}$, integration frequency: 45

[11] Total Light Transmittance

After the following apparatus was coordinated to a standard with a blank (state in which the apparatus has nothing mounted thereon), a film-shaped sample was attached to a dedicated attachment, and the average value of three measurements was read.

Apparatus: HGM-2DP manufactured by Suga Test Instruments Co., Ltd.

[12] Melt Viscosity

Using a B type viscometer (manufactured by TOKIMEC INC, MODEL: BBH), measurement was performed at 20 to 100 rpm on a rotor HH-1 with the sample heated to 150° C.

[13] Epoxy Equivalent

Using an automatic titration device (AT-5100 manufactured by KYOTO ELECTRONICS MANUFACTURING CO., LTD.), measurement was performed by a method as specified in JIS K 7236.

1. Production Example of Bisphenol

Example 1

In a glass reactor equipped with a stirrer, a heating and cooling device and a thermometer, 10 g (0.056 mol) of 9-fluorenone, 43.3 g (0.166 mol) of 2-benzyl-6-phenylphenol, 6.5 g (0.0342 mol) of para-toluenesulfonic acid monohydrate, 0.56 g (0.00277 mol) of dodecyl mercaptan and 56 g of toluene were added, then heated to 110° C., and stirred at this temperature for 3 hours. After stirring was completed, the reaction liquid was analyzed by high performance liquid chromatography, and the result showed a low bisphenol production ratio of 20.3%. Therefore, the internal pressure was reduced to 40 kPa, and the liquid was further stirred at this pressure for 6 hours while being refluxed and dehydrated at 90° C. After stirring was completed, the reaction liquid was analyzed by high performance liquid chromatography, and the result showed that the bisphenol production ratio was 89.9%.

A sodium hydroxide aqueous solution was added to the obtained reaction liquid to neutralize the reaction liquid, the aqueous layer was then removed, and the liquid was washed with water three times. Thereafter, the liquid was concentrated to partially distill off toluene, heptane was then added to the concentrate, the mixture was cooled to precipitate crystals, and the precipitated crystals were separated by filtration, and dried to obtain 18 g of bisphenol crystals (yield: 47% and HPLC purity: 95%).

Figure 2:
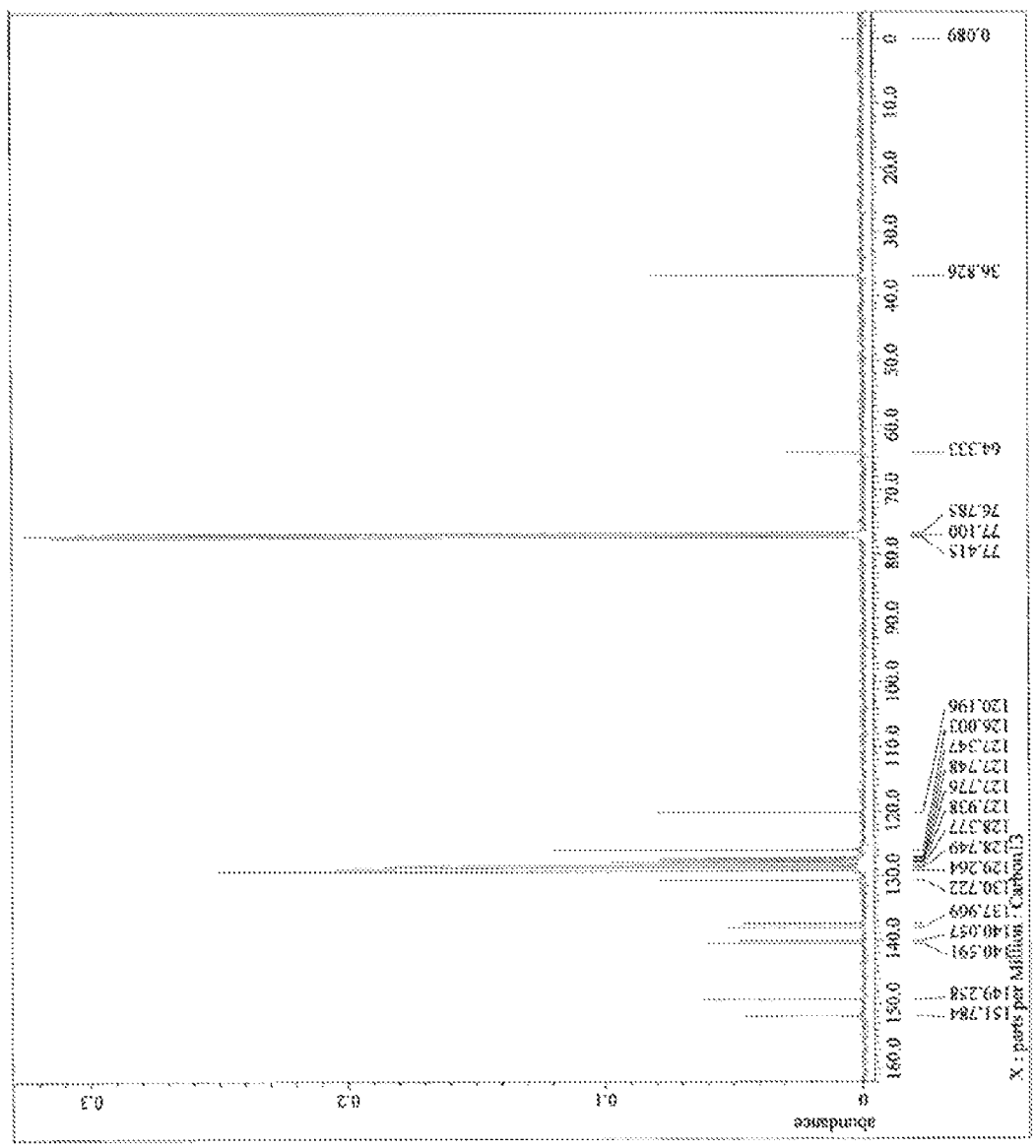
FIG. 2 shows a $^{13}$C-NMR chart of a bisphenol obtained in Example 1 and represented by the following formula (1-1).

The obtained bisphenol crystals were measured using $^1$H-NMR and $^{13}$C-NMR, and confirmed to have a structure represented by the following formula (1-1). The spectrum values in $^1$H-NMR and $^{13}$C-NMR are shown below, and the NMR charts for the obtained bisphenol represented by the following formula (1-1) are shown in FIGS. 1 and 2. The melting point, refractive index and 5% weight loss temperature of the obtained bisphenol represented by the following formula (1-1) were measured by the above-described methods. The results are shown in Table 1.

[Chemical Formula 9]

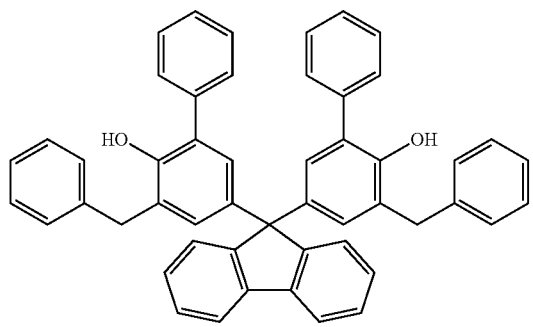

(1-1)

$^1$H-NMR (CDCl$_3$)

δ (ppm): 3.93 ppm (4H, s), 5.12 (2H, s), 6.91 (2H, d), 7.06 (2H, d), 7.15-7.40 (26H, m), 7.71 (2H, d).

$^{13}$C-NMR (CDCl$_3$)

δ (ppm): 36.83 ppm, 64.33 ppm, 120.20 ppm, 126.00 ppm, 127.19 ppm, 127.35 ppm, 127.68 ppm, 127.75 ppm, 127.78 ppm, 127.94 ppm, 128.38 ppm, 128.75 ppm, 129.26 ppm, 130.72 ppm, 137.39 ppm, 137.97 ppm, 140.06 ppm, 140.59 ppm, 149.26 ppm, 151.78 ppm.

Example 2

In a 500 ml glass reaction vessel equipped with a stirrer, a cooler and a thermometer, 40.03 g (0.222 mol) of 9-fluorenone, 173.20 g (0.666 mol) of 2-benzyl-6-phenylphenol, 2.26 g (0.011 mol) of 1-dodecanethiol, 26.20 g (0.138 mol) of para-toluenesulfonic acid monohydrate and toluene were added, then heated to 120° C., and stirred at this temperature for 4 hours while being refluxed and dehydrated. The obtained reaction liquid was cooled to 60° C., water was added, the mixture was neutralized with a 24 wt % sodium hydroxide aqueous solution, and cooled to room temperature, and the precipitated crystals were filtered. The obtained crystals were then washed with toluene twice, then washed with water three times, and dried under reduced pressure to obtain 104.70 g of white crystals of a bisphenol represented by the formula (1-1) (yield: 69.1% and HPLC purity: 98.6%).

Comparative Example 1

The melting point, refractive index and 5% weight loss temperature of a bisphenol represented by the formula (5) were measured by the above-described methods. The results are shown in Table 1.

Reference Example 1

In a glass reactor equipped with a stirrer, a heating and cooling device and a thermometer, 15 g of a bisphenol represented by the formula (5), 0.34 g of potassium carbonate, 6.6 g of ethylene carbonate and 15 g of methyl isoamyl ketone were added, heated to 120° C., and stirred at this temperature for 6 hours. Thereafter, the obtained reaction liquid was washed with water, crystallized, and dried to obtain 11 g of a crystal of a compound represented by the following formula (6) (yield: 64% and HPLC purity: 98%). The melting point, refractive index and 5% weight loss temperature of the obtained compound were measured by the above-described methods. The results are shown in Table 1.

[Chemical Formula 10]

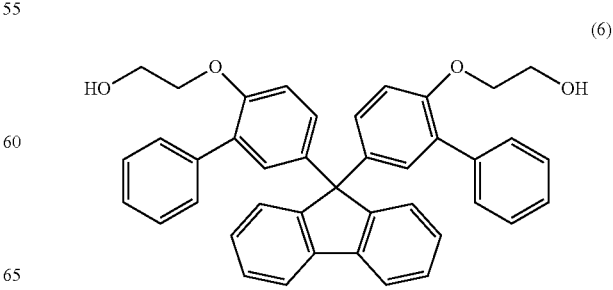

(6)

TABLE 1

|  | Example 1 | Comparative Example 1 | Reference Example 1 |
|---|---|---|---|
| Melting point (° C.) | 165 | 269 | 195 |
| Refractive index | 1.67 | 1.67 | 1.65 |
| 5% weight loss temperature (° C.) | 357 | 306 | 363 |

2. Production Example of Polyarylate Resin

Example 3

In a glass reactor equipped with a stirrer, a heating and cooling device and a thermometer, 88.3 g of water was added, 1.2 g (30 mmol) of sodium hydroxide, 5.0 g (7 mmol) of a bisphenol represented by the formula (1-1), 0.07 g (0.4 mmol) of p-tert-butylphenol as an end-capping agent and 0.02 g (0.05 mmol) of tributylbenzylammonium chloride as a polymerization catalyst were added, and the mixture was vigorously stirred to prepare an alkaline suspension liquid.

In another container, 0.77 g (3.8 mmol) of terephthalic acid chloride and 0.77 g (3.8 mmol) of isophthalic acid chloride were added, and dissolved in 68.3 g of methylene chloride. The methylene chloride solution was mixed with the previously prepared alkali suspension liquid with stirring to initiate polymerization. The polymerization reaction temperature was adjusted to be around 20° C. The polymerization was performed for 2 hours under stirring, stirring was then stopped, the reaction liquid was left standing to separate the aqueous phase and the organic phase, only the aqueous phase was removed from the reactor, 0.15 g of acetic acid and 110.0 g of water were added to the remaining organic phase, the mixture was stirred for 30 minutes, and left standing for perform separation again, and the aqueous phase was removed. This water-washing operation was repeated until the aqueous phase after washing with water had a pH of 7.

Figure 3:
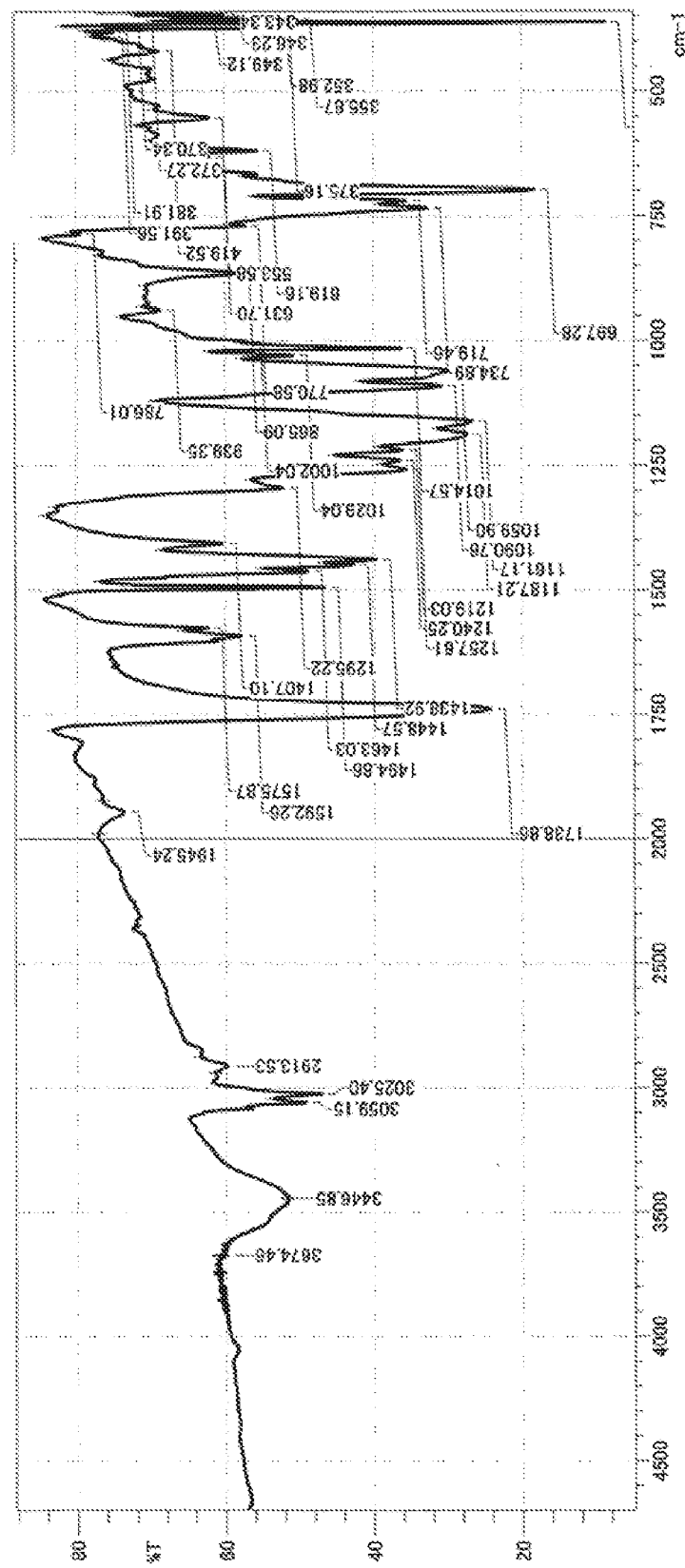
FIG. 3 shows an IR spectrum of a polyarylate resin which is obtained in Example 3 and which has a constituent unit derived from a bisphenol represented by the general formula (1) and a constituent unit derived from an aromatic dicarboxylic acid.

The obtained organic phase was gradually added to a vessel containing 200 g of methanol, so that the resin was precipitated, and the precipitated powdered resin was separated by filtration, and dried to obtain a polyarylate resin. FT-IR measurement of the obtained polyarylate resin was performed, and resultantly it was confirmed that an OH stretching vibration (3400 to 3600 cm$^{-1}$) derived from a bisphenol fluorene as a raw material disappeared, and a C—CO—O stretching vibration (1170 to 1260 cm$^{-1}$) existed. Thus, it was confirmed that a polyarylate resin having a constituent unit derived from a bisphenol represented by the general formula (1) and a constituent unit derived from an aromatic dicarboxylic acid had been produced. The IR spectrum of the obtained polyarylate resin is shown in FIG. 3.

The glass transition temperature (Tg), refractive index, fluidity and solvent solubility of the obtained polyarylate resin were measured by the above-described methods. The results are shown in Table 2. The obtained polyarylate resin was then dissolved in tetrahydrofuran (THF) to give a 10 wt % solution, a coating film having a thickness of about 900 μm was formed on a glass plate using an applicator, preliminarily dried under an environment of about 23° C. for 1 hour, then placed in a vacuum dryer, and heated stepwise to 40° C. for 30 minutes, 60° C. for 30 minutes and 80° C. for 30 minutes, so that the coating film was dried to obtain a transparent polyarylate resin film having a thickness of 90 μm. The total light transmittance of the obtained polyarylate resin film was measured. The results are shown in Table 2.

In a comparative example below, a polyarylate film resin was similarly prepared with the polyarylate resin dissolved in methylene chloride if it was not dissolved in THF.

Example 4

Except that only 1.5 g (7.6 mmol) of terephthalic acid chloride was used as an aromatic dicarboxylic acid derivative, the same procedure as in Example 3 was carried out to obtain a polyarylate resin. The solubility in various solvents, glass transition temperature (Tg), fluidity, refractive index and total light transmittance for the obtained polyarylate resin were measured in the same manner as in Example 3. The results are shown in Table 2.

Comparative Example 2

Except that the bisphenol used and the use amounts of the components in Example 3 were changed in accordance with the following, the same procedure as in Example 3 was carried out to obtain a polyarylate resin. The solubility in various solvents, Tg, fluidity, refractive index and total light transmittance for the obtained polyarylate resin were measured in the same manner as in Example 3. The results are shown in Table 2.

1.2 g (30 mmol) of sodium hydroxide→3.6 g (90 mmol) of sodium hydroxide 5.0 g (7 mmol) of bisphenol represented by the formula (1-1)→5.0 g (22 mmol) of bisphenol A 0.07 g (0.4 mmol) of p-tert-butylphenol→0.20 g (1.3 mmol) of p-tert-butylphenol 0.02 g (0.05 mmol) of tributylbenzylammonium chloride→0.05 g (0.15 mmol) of tributylbenzylammonium chloride 0.77 g (3.8 mmol) of terephthalic acid chloride→2.29 g (11.3 mmol) of terephthalic acid chloride 0.77 g (3.8 mmol) of isophthalic acid chloride→2.29 g (11.3 mmol) of isophthalic acid chloride Comparative Example 3

Except that the bisphenol used and the use amounts of the components in Example 3 were changed in accordance with the following, the same procedure as in Example 3 was carried out to obtain a polyarylate resin. The solubility in various solvents, Tg, fluidity, refractive index and total light transmittance for the obtained polyarylate resin were measured in the same manner as in Example 3. The results are shown in Table 2.

1.2 g (30 mmol) of sodium hydroxide→2.2 g (50 mmol) of sodium hydroxide 5.0 g (7 mmol) of bisphenol represented by the formula (1-1)→5.0 g (13 mmol) of 9,9-bis(4-hydroxy-3-methylphenyl)fluorene 0.07 g (0.4 mmol) of p-tert-butylphenol→0.12 g (0.8 mmol) of p-tert-butylphenol 0.02 g (0.05 mmol) of tributylbenzylammonium chloride→0.03 g (0.10 mmol) of tributylbenzylammonium chloride 0.77 g (3.8 mmol) of terephthalic acid chloride→1.38 g (6.8 mmol) of terephthalic acid chloride 0.77 g (3.8 mmol) of isophthalic acid chloride→1.38 g (6.8 mmol) of isophthalic acid chloride

TABLE 2

|  |  | Example 3 | Example 4 | Comparative Example 2 | Comparative Example 3 |
|---|---|---|---|---|---|
| Mw |  | 46,764 | 46,551 | 81,685 | 36,663 |
| Tg (° C.) |  | 189 | 190 | 193 | 288 |
| Fluidity (MFR) Load: 2.160 kg | 285° C. | 69 g/10 min | 68 g/10 min | Measurement impossible | Measurement impossible |
|  | 360° C. | 1400 g/10 min | 1388 g/10 min | 6 g/10 min | 0.03 g/10 min |
| Refractive index |  | 1.664 | 1.643 | 1.615 | 1.644 |
| Solvent solubility | Toluene | ○ | ○ | X | X |
|  | THF | ○ | ○ | X | Δ |
|  | Methylene chloride | ○ | ○ | ○ | X |
| Total light transmittance |  | 88% | 88% | 88% | 88% |

3. Production Example of (Meth)Acrylate Compound

Example 5

In a 500 ml glass reaction vessel equipped with a stirrer, a cooler and a thermometer, 60.00 g (0.088 mol) of a bisphenol represented by the formula (1-1), 0.12 g (0.00097 mol) of p-methoxyphenol, 19.56 g (0.19 mol) of triethylamine and toluene were added, and stirred at 25° C. Thereafter, 16.70 g (0.18 mol) of acrylic acid chloride was added, and the mixture was reacted for 2 hours while the above temperature was maintained.

After the reaction, the reaction liquid was analyzed by HPLC, and the result showed that a (meth) acrylate compound was produced in an amount of 96.9%.

The obtained reaction liquid was neutralized by adding 5% sodium bicarbonate aqueous solution thereto, then washed with water twice, and concentrated under reduced pressure to obtain 67.3 g of a (meth)acrylate compound (yield: 96.9% and HPLC purity: 97.0%).

Figure 4:
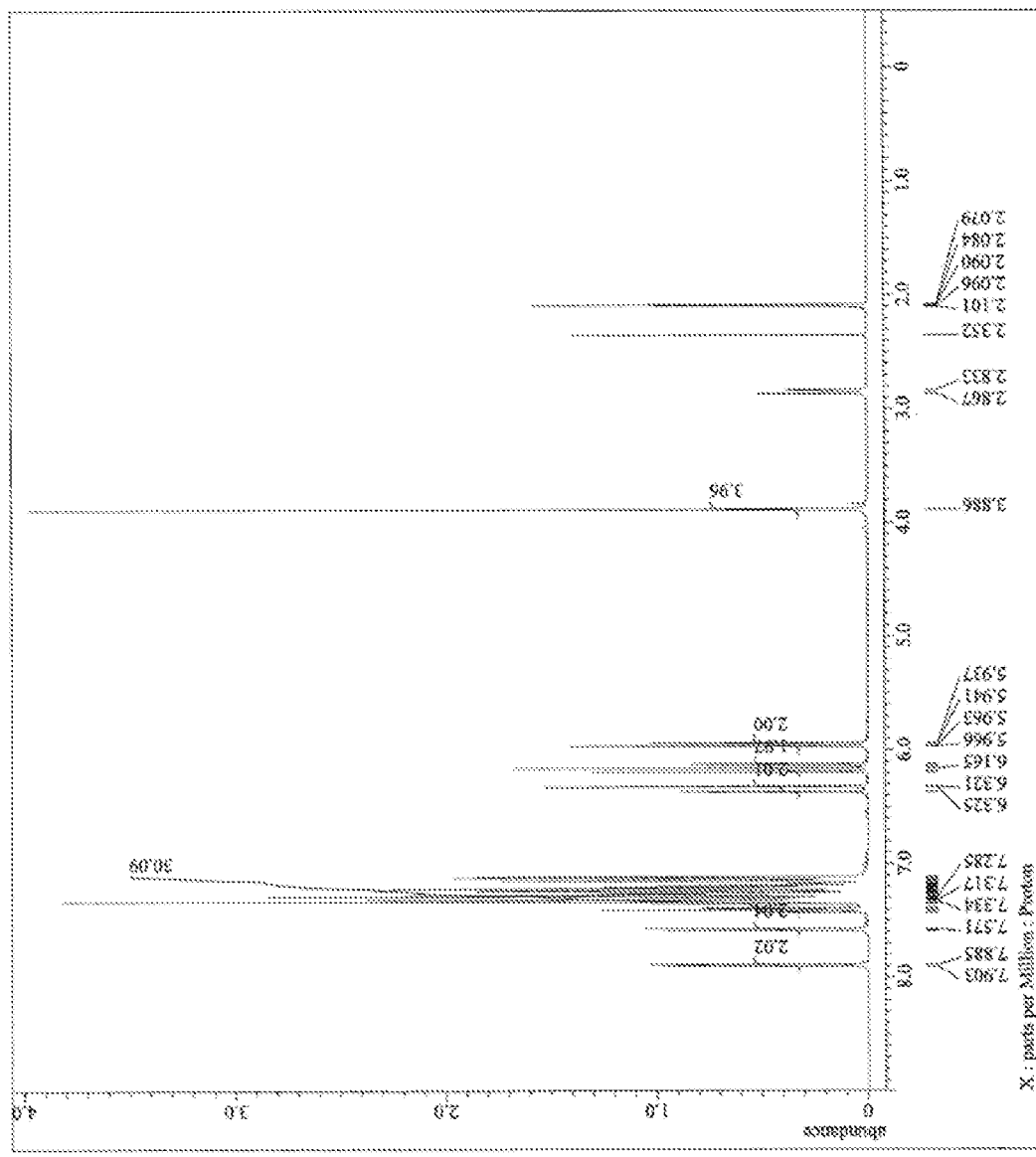
FIG. 4 shows a $^1$H-NMR chart of a (meth)acrylate compound obtained in Example 5 and represented by the following formula (3-1).
Figure 5:
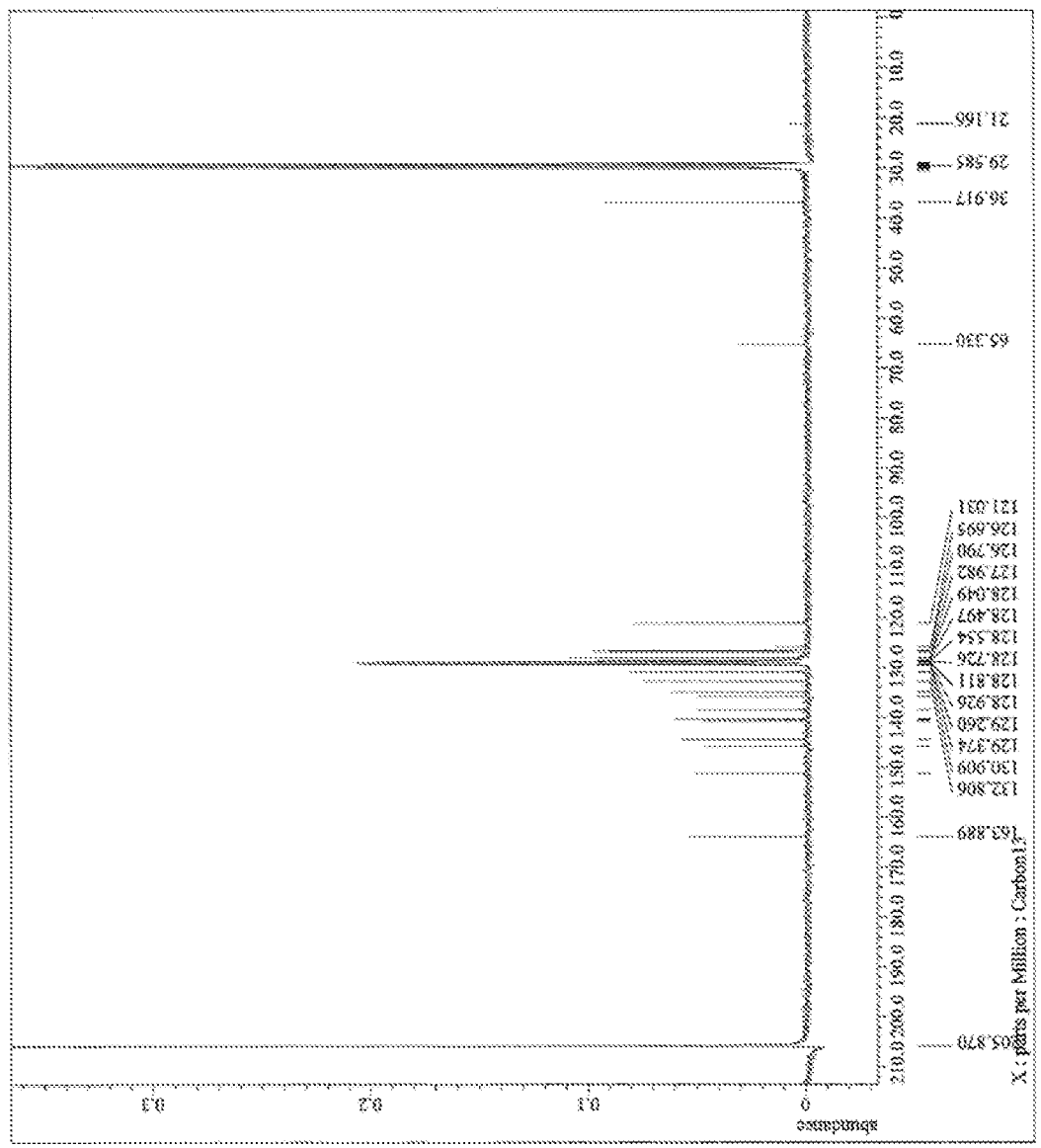
FIG. 5 shows a $^{13}$C-NMR chart of a (meth)acrylate compound obtained in Example 5 and represented by the following formula (3-1).
Figure 6:
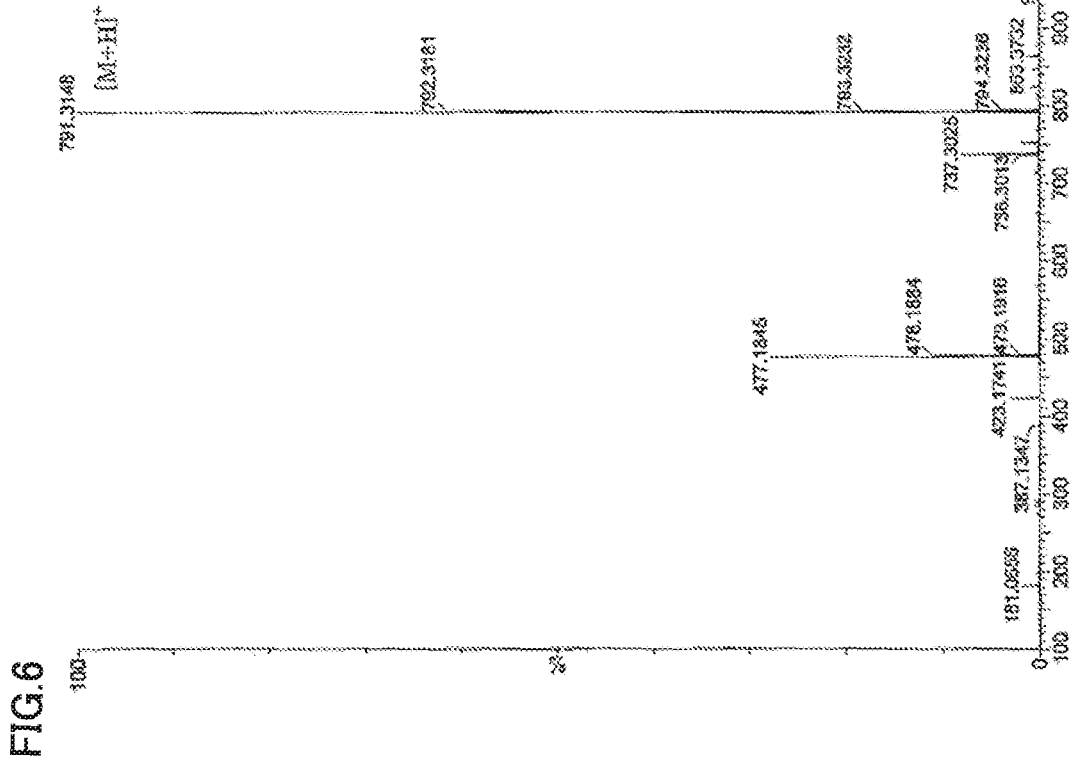
FIG. 6 shows a mass spectrometric analysis chart of a (meth)acrylate compound obtained in Example 5 and represented by the following formula (3-1).

The obtained (meth)acrylate compound was measured using $^1$H-NMR, $^{13}$C-NMR and LC-MS, and confirmed to have a structure represented by the following formula (3-1). The spectrum values in $^1$H-NMR, $^{13}$C-NMR and LC-MS are shown below, and the NMR charts and mass spectrometric analysis chart for the obtained (meth)acrylate compound represented by the following formula (3-1) are shown in FIGS. 4 to 6. In addition, Table 3 shows the measurement results of the refractive index, Abbe number, melting point or glass transition temperature (Tg), and solubility in the diluent.

[Chemical Formula 11]

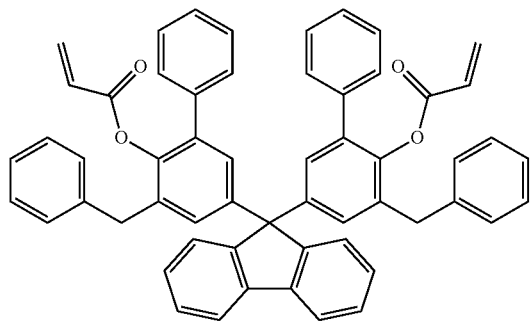

(3-1)

$^1$H-NMR (CD$_3$COCD$_3$)
δ (ppm): 3.89 ppm (4H, s), 5.95 ppm (2H, dd, J=1.2, 8.8), 6.12-6.19 ppm (2H, m), 6.32-6.37 ppm (2H, m), 7.11-7.43 ppm (30H, m), 7.89 ppm (2H, d, J=7.2).

$^{13}$C-NMR (CD$_3$COCD$_3$)
δ (ppm): 21.17 ppm, 30.53 ppm, 36.92 ppm, 65.33 ppm, 121.03 ppm, 125.87 ppm, 126.69 ppm, 126.79 ppm, 127.98 ppm, 128.05 ppm, 128.50 ppm, 128.55 ppm, 128.73 ppm, 128.81 ppm, 128.93 ppm, 129.26 ppm, 129.37 ppm, 129.51 ppm, 130.91 ppm, 132.81 ppm, 134.87 ppm, 135.80 ppm, 138.45 ppm, 140.30 ppm, 140.68 ppm, 144.40 ppm, 145.78 ppm, 151.26 ppm, 163.89 ppm.

Mass spectrometric analysis value: 791.3148 (calculated molecular weight of the compound represented by the formula (3-1) (TOF MS APCI$^+$; C$_{57}$H$_{42}$O$_4$+H): 791.3083).

Comparative Example 4: Production Example of Acrylate Compound Represented by Formula (7)

[Chemical Formula 12]

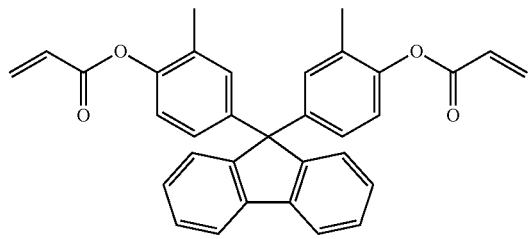

(7)

In a 500 ml glass reaction vessel equipped with a stirrer, a cooler and a thermometer, 60.00 g (0.16 mol) of 9,9-bis(4-hydroxy-3-methylphenyl)fluorene, 0.22 g (0.0017 mol) of p-methoxyphenol, 35.29 g (0.35 mol) of triethylamine and toluene were added, and stirred at 25° C. Thereafter, 30.13 g (0.33 mol) of acrylic acid chloride was added, and the mixture was reacted for 2 hours while the above temperature was maintained.

After the reaction, the reaction liquid was subjected to HPLC analysis, and the result showed that an acrylate compound represented by the formula (7) was produced in an amount of 89.6%.

The obtained reaction liquid was neutralized by adding 5% sodium bicarbonate aqueous solution thereto, then washed with water twice, and concentrated under reduced pressure to obtain 61.7 g of an acrylate compound represented by the formula (7) (yield: 80.0% and HPLC purity: 93.0%).

Table 3 shows the measurement results of the refractive index, Abbe number, melting point or glass transition temperature (Tg), and solubility in the diluent for the obtained acrylate compound represented by the formula (7).

Comparative Example 5: Production Example of Acrylate Compound Represented by Formula (8)

[Chemical Formula 13]

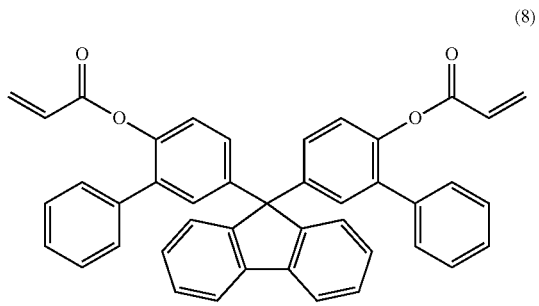

(8)

In a 500 ml glass reaction vessel equipped with a stirrer, a cooler and a thermometer, 60.00 g (0.12 mol) of 9,9'-bis(4-hydroxy-3-phenylphenyl)fluorene, 0.16 g (0.0013 mol) of p-methoxyphenol, 26.57 g (0.26 mol) of triethylamine and toluene were added, and stirred at 25° C. Thereafter, 22.69 g (0.25 mol) of acrylic acid chloride was added, and the mixture was reacted for 2 hours while the above temperature was maintained.

After the reaction, the reaction liquid was subjected to HPLC analysis, and the result showed that an acrylate compound represented by the formula (8) was produced in an amount of 90.4%.

The obtained reaction liquid was neutralized by adding 5% sodium bicarbonate aqueous solution thereto, then washed with water twice, and concentrated under reduced pressure to obtain 19.3 g of an acrylate compound represented by the formula (8) (yield: 26.4% and HPLC purity: 96.5%).

Table 3 shows the measurement results of the refractive index, Abbe number, melting point or glass transition temperature (Tg), and solubility in the diluent for the obtained acrylate compound represented by the formula (8).

Comparative Example 6: Production Example of Acrylate Compound Represented by Formula (9)

[Chemical Formula 14]

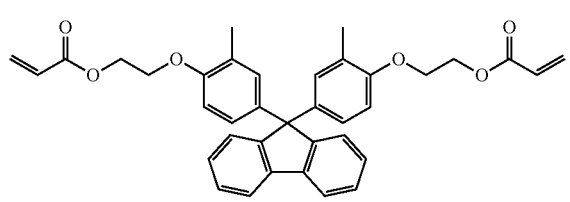

(9)

In a 500 ml glass reaction vessel equipped with a stirrer, a cooler and a thermometer, 60.00 g (0.13 mol) of 9,9-bis(4-(2-hydroxyethoxy)-3-methylphenyl)fluorene, 3.18 g (0.017 mol) of p-toluenesulfonic acid, 0.32 g (0.0026 mol) of p-methoxyphenol, 24.09 g (0.33 mol) of acrylic acid and toluene were added, and subjected to a dehydration esterification reaction while being refluxed at 110° C. to 115° C. until a theoretical dehydration amount was obtained.

After the reaction, the reaction liquid was subjected to HPLC analysis, and the result showed that an acrylate compound represented by the formula (9) was produced in an amount of 88.6%.

The obtained reaction liquid was neutralized by adding 5% sodium bicarbonate aqueous solution thereto, then washed with a saline solution twice, and concentrated under reduced pressure to obtain 66.4 g of an acrylate compound represented by the formula (9) (yield: 89.9% and HPLC purity: 88.6%).

Table 3 shows the measurement results of the refractive index, Abbe number, melting point or glass transition temperature (Tg), and solubility in the diluent for the obtained acrylate compound represented by the formula (9).

Reference Example 2: Production Example of Acrylate Compound Represented by Formula (10)

[Chemical Formula 15]

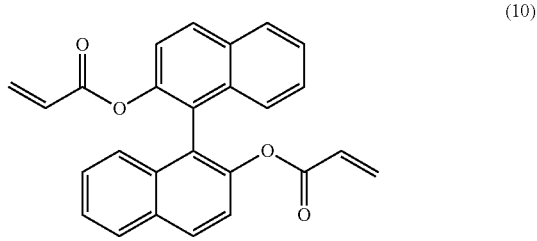

(10)

In a 500 ml glass reaction vessel equipped with a stirrer, a cooler and a thermometer, 60.00 g (0.21 mol) of 1,1'-bi-2-naphthol, 0.29 g (0.0023 mol) of p-methoxyphenol, 46.65 g (0.46 mol) of triethylamine and toluene were added, and stirred at 25° C. Thereafter, 39.83 g (0.44 mol) of acrylic acid chloride was added, and the mixture was reacted for 2 hours while the above temperature was maintained.

After the reaction, the reaction liquid was subjected to HPLC analysis, and the result showed that an acrylate compound represented by the formula (10) was produced in an amount of 93.1%.

The obtained reaction liquid was neutralized by adding 5% sodium bicarbonate aqueous solution thereto, then washed with water twice. Thereafter, the liquid was cooled to 0° C. to precipitate crystals, and the precipitated crystals were filtered and dried to obtain 27.9 g of an acrylate compound represented by the formula (10) (yield: 33.7% and HPLC purity: 98.0%).

Table 3 shows the measurement results of the refractive index, Abbe number, melting point or glass transition temperature (Tg), and solubility in the diluent for the obtained acrylate compound represented by the formula (10).

TABLE 3

|  |  |  | Example 5 | Comparative Example 4 | Comparative Example 5 | Comparative Example 6 | Reference Example 2 |
|---|---|---|---|---|---|---|---|
| Refractive index |  |  | 1.633 | 1.606 | 1.644 | 1.591 | 1.632 |
| Abbe number |  |  | 19.7 | 25.5 | 21.4 | 23.1 | 19.0 |
| Melting point (° C.) |  |  | None | 231 | 223 | None | 131 |
| Tg (° C.) |  |  | 32.4 | None | None | 0.0 | None |
| Solubility (30 mass % concentration) | Solvent | PGME | ○ | x | x | x | x |
|  |  | PGMEA | ○ | x | x | ○ | x |
|  |  | MEK | ○ | x | x | ○ | ○ |
|  |  | EA | ○ | x | x | ○ | ○ |
|  | Monofunctional acrylate | OPPEA | ○ | x | x | ○ | x |
|  |  | POB-A | ○ | x | x | ○ | x |

<Abbreviations of Diluents in Table 3>
PGME: propylene glycol monomethyl ether
PGMEA: propylene glycol monomethyl ether acetate
MEK: methyl ethyl ketone
EA: ethyl acetate
OPPEA: 2-phenylphenoxyethyl acrylate (manufactured by Shin-Nakamura Chemical Co., Ltd.)
POB-A: m-phenoxybenzyl acrylate (manufactured by Kyoeisha Chemical Co., Ltd.)

4. Production Example of Epoxy Resin

Example 6

In a 500 ml glass reaction vessel equipped with a stirrer, a cooler and a thermometer, 50.02 g (0.073 mol) of a bisphenol represented by the formula (1-1), 203.36 g (2.197 mol) of epichlorohydrin and 1.67 g (0.007 mol) of benzyltriethylammonium chloride were added under a nitrogen atmosphere, heated to 70° C., and then stirred at this temperature for 3.5 hours. After stirring, the reaction liquid was analyzed by HPLC, and the result showed that the residual ratio of the bisphenol represented by the formula (1-1) as a raw material was less than or equal to 0.5%.

After completion of the reaction, the obtained reaction liquid was heated to 120° C., and excessive epichlorohydrin etc. was distilled off under a reduced internal pressure of 10 mmHg to obtain a concentrate. Thereafter, the concentrate was cooled to 110° C., toluene was added to and dissolved in the obtained concentrate, the mixture was cooled to 60° C., 61.30 g (0.366 mol) of a 24 wt % sodium hydroxide aqueous solution was then added at 60° C., and the mixture was stirred at this temperature for 3.5 hours. After stirring, the mixture was left standing to remove the lower layer by liquid separation.

Thereafter, neutralization was performed by adding an acid, and the aqueous layer was removed by liquid separation. The organic layer was then washed with water, activated carbon was then added to the organic layer, and the mixture was stirred at 60° C. for 2 hours, then filtered to remove insoluble components and activated carbon, and then concentrated under reduced pressure to distill off toluene, thereby obtaining 56.18 g of an epoxy resin as a light yellow solid.

Figure 7:
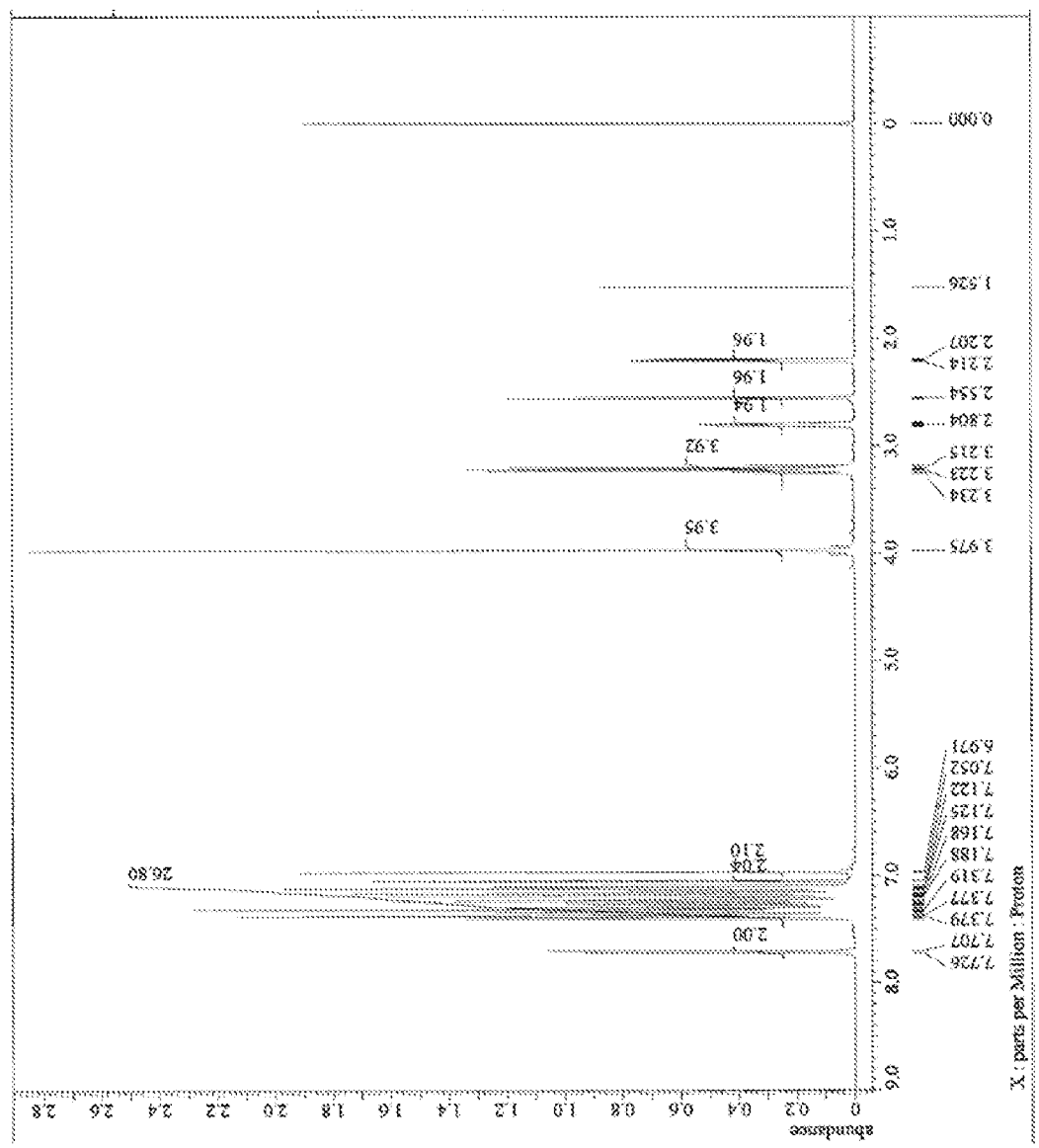
FIG. 7 shows a $^1$H-NMR chart of an epoxy resin obtained in Example 6 and represented by the following formula (4-1).
Figure 8:
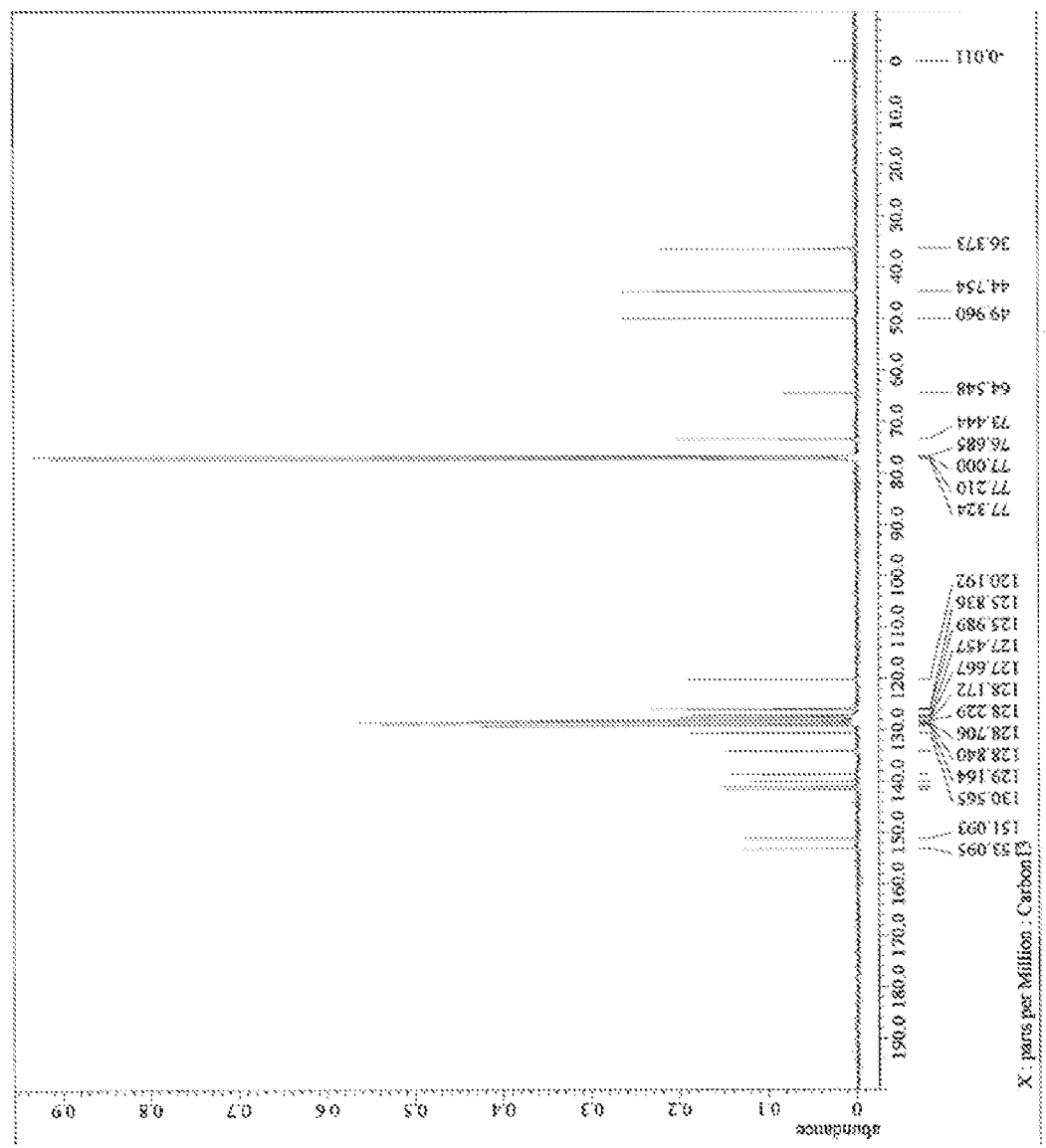
FIG. 8 shows a $^{13}$C-NMR chart of an epoxy resin obtained in Example 6 and represented by the following formula (4-1).
Figure 9:
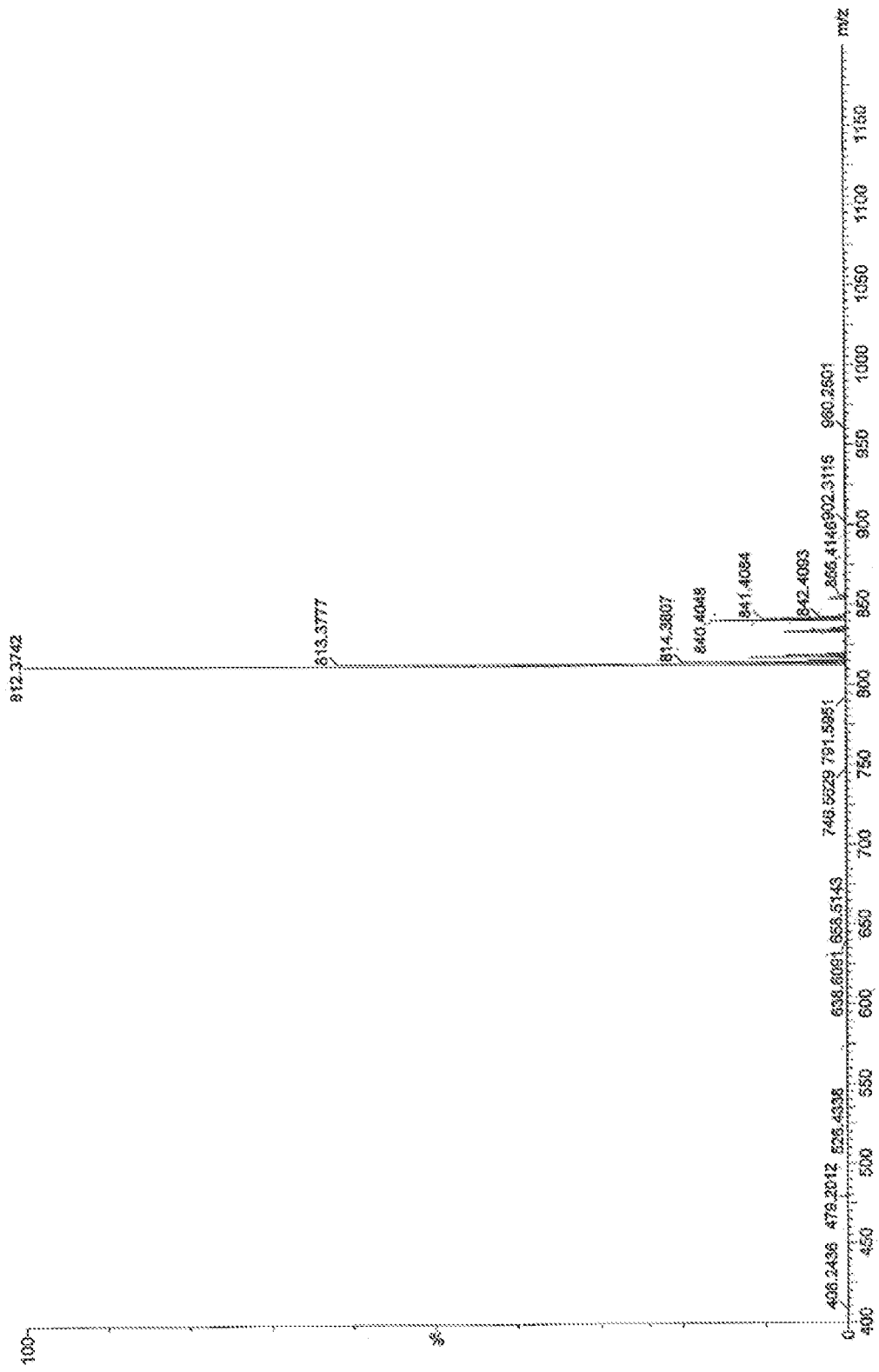
FIG. 9 shows a mass spectrometric analysis chart of an epoxy resin obtained in Example 6 and represented by the following formula (4-1).

The obtained epoxy resin was measured using $^1$H-NMR, $^{13}$C-NMR and LC-MS, and confirmed to have a structure represented by the following formula (4-1). The spectrum values in $^1$H-NMR, 13C-NMR and LC-MS are shown below, and the NMR charts and mass spectrometric analysis chart for the obtained epoxy resin represented by the following formula (4-1) are shown in FIGS. 7 to 9. In addition, the obtained epoxy resin was analyzed by HPLC, and the result showed that the content (HPLC purity) of the epoxy resin represented by the following formula (4-1) wherein p=0 was 96.1%, and the epoxy equivalent was 402 g/eq. The measurement results of the solvent solubility, melt viscosity at 150° C., refractive index, Abbe number and 5% weight loss temperature are shown in Table 4.

[Chemical Formula 16]

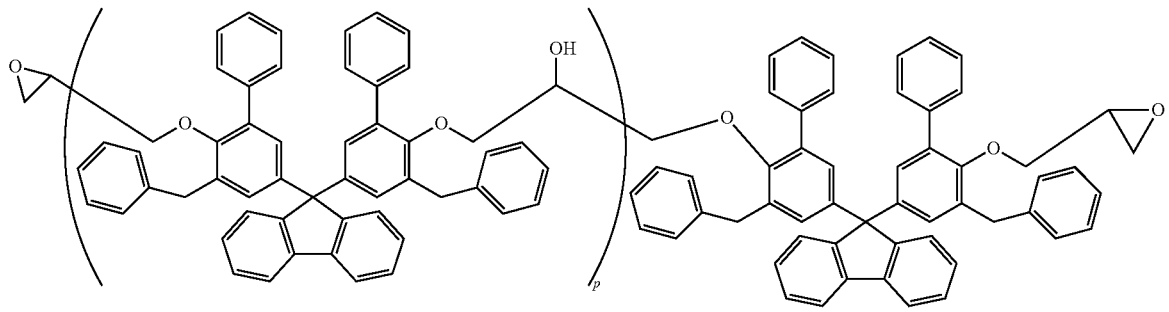

(4-1)

(where p represents 0 or an integer of 1 or more).

$^1$H-NMR (CDCl$_3$)

δ (ppm): 2.21 (dd, J=2.80, J=2.0, 2H), 2.55 (t, J=4.00, 2H), 2.80 (m, 2H), 3.17-3.27 (m, 4H), 3.98 (s, 4H), 6.97 (d, J=2.40, 2H), 7.05 (d, J=2.00, 2H), 7.10-7.40 (m, 26H), 7.72 (d, J=7.60, 2H).

13C-NMR (CDCl3)

δ (ppm): 36.37, 44.75, 49.96, 64.55, 73.44, 120.19, 125.84, 125.99, 127.12, 127.46, 127.67, 128.17, 128.23, 128.51, 128.71, 128.84, 129.16, 130.57, 134.04, 134.25, 138.60, 140.02, 140.99, 141.58, 151.09, 153.09.

Mass spectrometric analysis value: 812.3742 (calculated molecular weight of the epoxy resin represented by the formula (4-1) (TOF MS ESI$^+$; $C_{55}H_{42}O_4$+$NH_4$): 812.3740).

Comparative Example 7: Production Example of Epoxy Resin Containing Constituent Unit Derived from Bisphenol Represented by Formula (5) in Main Chain (Fluorene-Based Epoxy Resin Represented by Formula (11))

[Chemical Formula 17]

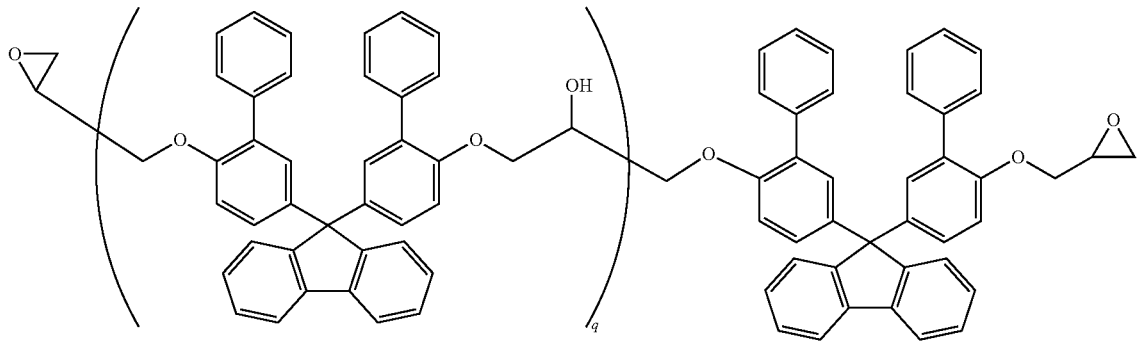

(11)

(where q represents 0 or an integer of 1 or more).

In a 1000 ml glass reaction vessel equipped with a stirrer, a cooler and a thermometer, 150.07 g (0.298 mol) of a bisphenol represented by the formula (5), 828.40 g (8.953 mol) of epichlorohydrin and 6.85 g (0.030 mol) of benzyltriethylammonium chloride were added under a nitrogen atmosphere, heated to 70° C., and then stirred at this temperature for 3 hours. After stirring, the reaction liquid was analyzed by HPLC, and the result showed that the residual ratio of the bisphenol represented by the formula (5) as a raw material was less than or equal to 0.5%.

The obtained reaction liquid was heated to 160° C., and excessive epichlorohydrin etc. was distilled off under a reduced internal pressure of 20 mmHg to obtain a concentrate. Thereafter, the concentrate was cooled to 100° C., toluene was added to and dissolved in the concentrate, the mixture was cooled to 60° C., 248.10 g (2.238 mol) of a 24 wt % sodium hydroxide aqueous solution was then added at this temperature, and the mixture was stirred at this temperature for 4 hours. After stirring, the mixture was left standing to remove the lower layer by liquid separation.

Thereafter, neutralization was performed by adding water and an acid, and the aqueous layer was removed by liquid separation. The organic layer was then washed with water, activated carbon was then added to the organic layer, and the mixture was stirred at 60° C. for 2 hours, then filtered to remove insoluble components and activated carbon, and then concentrated under reduced pressure to distill off toluene, thereby obtaining 164.34 g of an epoxy resin as a yellow solid, which is represented by the formula (11).

The obtained epoxy resin represented by the formula (11) was analyzed by HPLC, and the result showed that the content (HPLC purity) of the epoxy resin represented by the formula (11) wherein q=0 was 86.8%, and the epoxy equivalent was 326 g/eq. The measurement results of the solvent solubility, melt viscosity at 150° C., refractive index, Abbe number and 5% weight loss temperature are shown in Table 4.

Comparative Example 8: Physical Property Values of Fluorene-Based Epoxy Resin Represented by Formula (12)

[Chemical Formula 18]

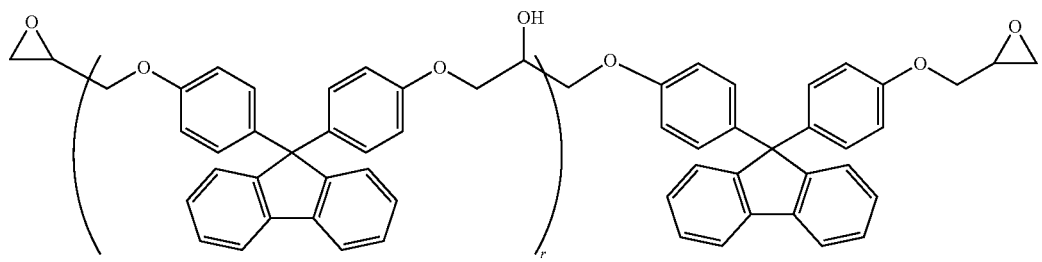

(12)

(r is 0 or an integer of 1 or more).

The solvent solubility, melt viscosity at 150° C., refractive index, Abbe number, and 5% weight loss temperature were measured for a bisphenol fluorene epoxy resin represented by the formula (12) (manufactured by Tokyo Chemical Industry Co., Ltd., white crystal, content of epoxy resin represented by the formula (12) wherein r=0 (HPLC purity): 97.3%, epoxy equivalent: 234 g/eq). The results are shown in Table 4.

TABLE 4

|  | Example 6 | Comparative Example 7 | Comparative Example 8 |
|---|---|---|---|
| Epoxy equivalent (g/eq) | 402 | 326 | 234 |
| Solvent solubility Toluene | ○ | X | X |
| MEK | ○ | X | X |
| PGMEK | ○ | X | X |
| MBA | ○ | X | X |
| Melt viscosity at 150° C. (mPa · s) | 2110 | 10700 | Crystal insoluble |
| Refractive index | 1.64 | 1.64 | 1.62 |
| Abbe number | 21.0 | 20.4 | 24.3 |
| 5% weight loss temperature (° C.) | 368 | 379 | 339 |

<Abbreviations of Solvents in Table 4>
MEK: methyl ethyl ketone
PGMEK: propylene glycol monomethyl ether acetate
MBA: 3-methoxybutyl acetate

The invention claimed is:

1. A bisphenol represented by a general formula (1) below:

[Chemical Formula 1]

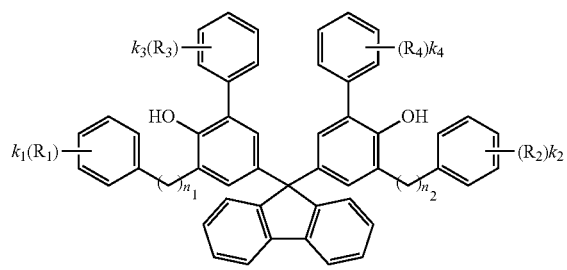

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different).

2. The bisphenol according to claim 1, wherein in the general formula (1), $k_1$ to $k_4$ each represent 0, and $n_1$ and $n_2$ each represent 1.

3. A method for producing the bisphenol according to claim 1, the method comprising, in presence of an acid, reacting 9-fluorenone with a phenol compound represented by a general formula (2) below:

[Chemical Formula 2]

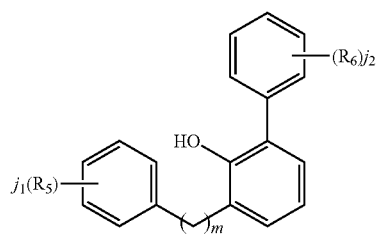

(2)

(where $R_5$ and $R_6$ are the same or different, and each represent an alkyl group, an aryl group or a halogen atom, m represents an integer of 1 to 4, and $j_1$ and $j_2$ are the same or different, and each represent 0 or an integer of 1 to 4; and when $j_1$ and/or $j_2$ are (is) 2 or more, corresponding $R_5$ and/or $R_6$ may be the same or different).

4. A polyarylate resin having a constituent unit derived from a bisphenol represented by a general formula (1) below:

[Chemical Formula 3]

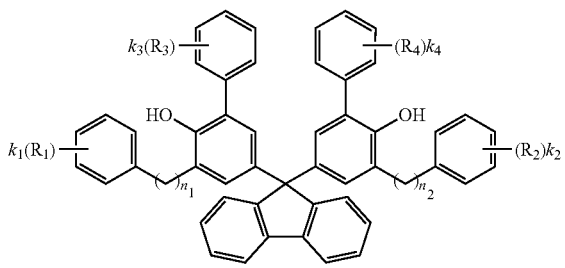

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different), and a constituent unit derived from an aromatic dicarboxylic acid.

5. The polyarylate resin according to claim 4, wherein in the general formula (1), $k_1$ to $k_4$ each represent 0, and $n_1$ and $n_2$ each represent 1.

6. A molded product comprising the polyarylate resin according to claim 4.

7. The molded product according to claim 6, wherein the molded product is an optical member.

8. A method for producing the polyarylate resin according to claim 4, the method comprising polymerizing the bisphenol and the aromatic dicarboxylic acid or a derivative of the aromatic dicarboxylic acid.

9. A (meth)acrylate compound represented by a general formula (3) below:

[Chemical Formula 4]

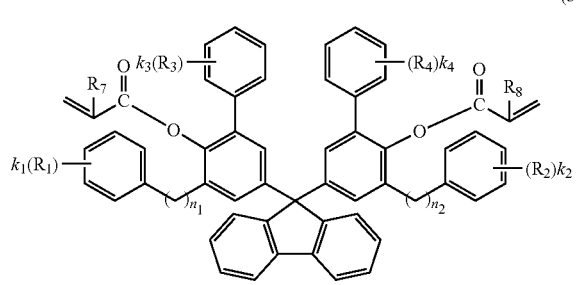

(3)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different; and $R_7$ and $R_8$ are the same or different, and each represent a hydrogen atom or a methyl group).

10. The (meth)acrylate compound according to claim 9, wherein in the general formula (3), $k_1$ to $k_4$ each represent 0, and $n_1$ and $n_2$ each represent 1.

11. A curable composition comprising the (meth)acrylate compound according to claim 9.

12. A cured product obtained by curing the curable composition according to claim 11.

13. A molded product comprising the cured product according to claim 12.

14. The molded product according to claim 13, wherein the molded product is an optical member.

15. A method for producing the (meth)acrylate compound according to claim 9, the method comprising reacting a (meth)acrylic acid with a bisphenol represented by a general formula (1) below:

[Chemical Formula 5]

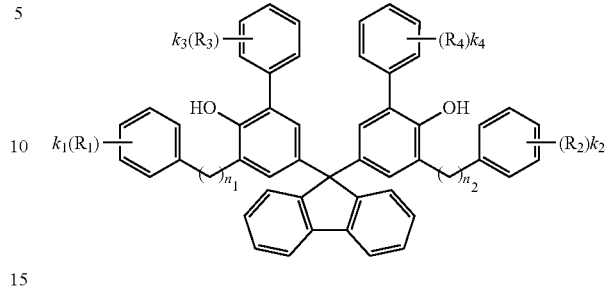

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different).

16. An epoxy resin comprising in a main chain a constituent unit derived from a bisphenol represented by a general formula (1) below:

[Chemical Formula 6]

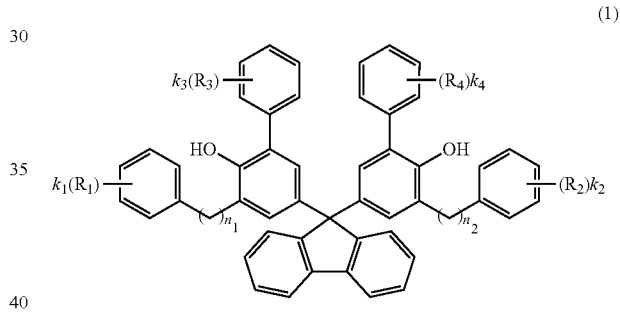

(1)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; and when at least one of $k_1$ to $k_4$ is 2 or more, corresponding $R_1$ to $R_4$ may be the same or different).

17. The epoxy resin according to claim 16, which is represented by a general formula (4) below:

[Chemical Formula 7]

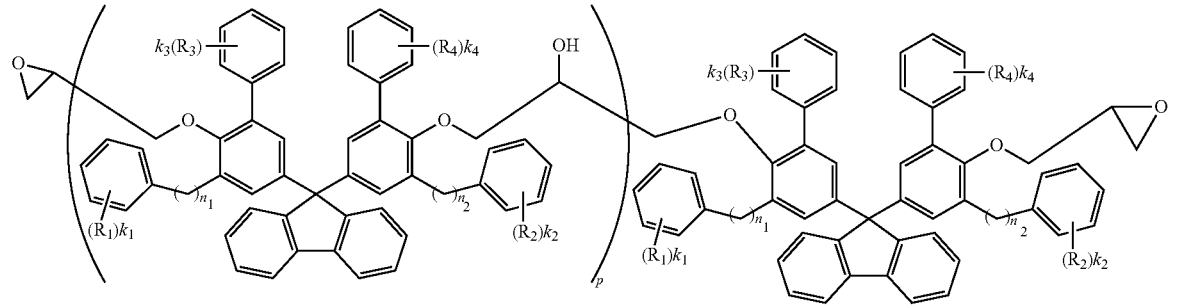

(4)

(where $R_1$ to $R_4$ are the same or different, and each represent an alkyl group, an aryl group or a halogen atom, $n_1$ and $n_2$ are the same or different, and each represent an integer of 1 to 4, and $k_1$ to $k_4$ are the same or different, and each represent 0 or an integer of 1 to 4; when at least one of $k_1$ to $k_4$ is 2 or more, corresponding $R_1$ to $R_4$ may be the same or different; and p represents 0 or an integer of 1 or more).

18. The epoxy resin according to claim 17, wherein in the general formula (4), $k_1$ to $k_4$ each represent 0, and $n_1$ and $n_2$ each represent 1.

19. A method for producing the epoxy resin according to claim 16, the method comprising reacting the bisphenol with epihalohydrin.

20. A resin composition comprising the epoxy resin according to claim 16.

21. A cured product obtained by curing the resin composition according to claim 20.

22. A molded product comprising the cured product according to claim 21.

23. The molded product according to claim 22, wherein the molded product is an optical member.

* * * * *